United States Patent [19]

Kamboj et al.

[11] Patent Number: 5,576,205
[45] Date of Patent: Nov. 19, 1996

[54] KAINATE-BINDING HUMAN CNS RECEPTORS OF THE EAA1 FAMILY

[75] Inventors: Rajender Kamboj, Mississauga; Stephen L. Nutt, Etobicoke; Lee Shekter, Toronto; Michael A. Wosnick, Thornhill, all of Canada

[73] Assignee: Allelix Biopharmaceuticals, Inc., Missassauga, Canada

[21] Appl. No.: 185,232

[22] Filed: Jan. 24, 1994

Related U.S. Application Data

[63] Continuation of Ser. No. 750,090, Aug. 26, 1991, abandoned.

[51] Int. Cl.$^6$ .................. C12N 1/21; C12N 5/10; C12N 15/12; C12N 15/79
[52] U.S. Cl. .................. 435/240.2; 435/240.4; 435/252.3; 435/320.1; 536/23.5; 536/24.31
[58] Field of Search .................. 435/6, 91.2, 69.1, 435/172.3, 240.2, 320.1, 240.4, 252.3; 530/350; 536/23.5, 24.31

[56] References Cited

FOREIGN PATENT DOCUMENTS

WO91/06648  5/1991  WIPO .

OTHER PUBLICATIONS

Hollmann et al, Nature (1989) 342:643.
Keinanen et al, Science (1990) 249:556.
Boulter et al, Science (1990) 249:1033.
Bettler et al, Neuron (1990) 5:583.
Sommer et al, Science (1990) 249:1580.
Monyer et al, Neuron (1991) 6:799.
Nakanishi et al, Neuron (1990) 5:569.
Hollmann et al, Science (1991) 252:851.
Verdoorn et al, Science (1991) 252:1715.
Egebjerg et al, Nature (1991) 351:745.
Wada et al, Nature (1991) 342:684.
Gregor et al, Nature (1989) 342:689.
Werner et al, Nature (1991) 351:742.
Barnett et al, Nucleic Acids Res. (1990) 18(10):3094.
William Sun, et al., "Molecular cloning, chromosomal mapping, and functional expression of human brain glutamate receptors"; Proc. Natl. Acad. Sci. USA, vol. 89, pp. 1443–1447, Feb. 1992.
Carmie Puckett, et al., "Molecular cloning and chromosomal localization of one of the human glutamate receptor genes"; Proc. Natl. Acad. Sci. USA, vol. 88, pp. 7557–7561, Sep. 1991.
Suggs, S. V. et al. *PNAS* 78(11):6613–6617 (1981).
Lee, C. C. et al. *Science* 239:1288–1291 (1988).

*Primary Examiner*—Dian C. Jacobson
*Attorney, Agent, or Firm*—Foley & Lardner

[57] ABSTRACT

Neurotransmission by excitatory amino acids (EAAs) such as glutamate is mediated via membrane-bound surface receptors. DNA coding for one family of these receptors, of the kainate binding type of EAA receptors, has now been isolated and the receptor protein characterized. Herein described are recombinant cell lines which produce the EAA receptor as a heterologous membrane-bound product. Also described are related aspects of the invention, which are of commercial significance. Included is use of the cell lines as a tool for discovery of compounds which modulate EAA receptor stimulation.

26 Claims, 14 Drawing Sheets

(LINEAR) MAP OF HumEAAIa

FIG.1(a)

```
            EcoRI
            |
    1   GAATTCCCTGAGTGCCTACTATGTGCCAGCCTGTGCTAGGCACTGAGGACACAGGTGGAA
        ------------+---------+---------+---------+---------+---------+   60
        CTTAAGGGACTCACGGATGATACACGGTCGGACACGATCCGTGACTCCTGTGTCCACCTT

HphI
                              |
    61  AAGCCCGAATTGCTCCCTGCTCTCCTGGCGCTCATCACCCCGGAGAGTTATGTCATGCCC
        ------------+---------+---------+---------+---------+---------+   120
        TTCGGGCTTAACGAGGGACGAGAGGACCGCGAGTAGTGGGGCCTCTCAATACAGTACGGG

121 AGGCCAGCAGGGGGCTCCATGAGGATTCATAGAAGATGCCCCGCGTCTCGGCGCCTTTGG
        ------------+---------+---------+---------+---------+---------+   180
        TCCGGTCGTCCCCCGAGGTACTCCTAAGTATCTTCTACGGGGCGCAGAGCCGCGGAAACC

M   P   R   V   S   A   P   L   V
                                       -20                     -15
                                                  PstI
                                                  |
    181 TGCTGCTTCCTGCGTGGCTCGTGATGGTCGCCTGCAGCCCGCACTCCTTGAGGATCGCTG
        ------------+---------+---------+---------+---------+---------+   240
        ACGACGAAGGACGCACCGAGCACTACCAGCGGACGTCGGGCGTGAGGAACTCCTAGCGAC

L   L   P   A   W   L   V   M   V   A   C   S   P   H   S   L   R   I   A   A    9
                -10                  -5               | Mature N-terminal
                      NcoI                                          HphI
                      |                                             |
    241 CTATCTTGGACGACCCCATGGAGTGCAGCAGAGGGGAGCGGCTCTCCATCACCCTGGCCA
        ------------+---------+---------+---------+---------+---------+   300
        GATAGAACCTGCTGGGGTACCTCACGTCGTCTCCCCTCGCCGAGAGGTAGTGGGACCGGT 10  I   L   D   D   P   M   E   C   S   R   G   E   R   L   S   I   T   L   A   K   29

301 AGAACCGCATCAACCGCGCTCCTGAGAGGCTGGGCAAGGCCAAGGTCGAAGTGGACATCT
        ------------+---------+---------+---------+---------+---------+   360
        TCTTGGCGTAGTTGGCGCGAGGACTCTCCGACCCGTTCCGGTTCCAGCTTCACCTGTAGA

30  N   R   I   N   R   A   P   E   R   L   G   K   A   K   V   E   V   D   I   F
                                                                    PstI
                                                                    |
    361 TTGAGCTTCTCAGAGACAGCGAGTACGAGACTGCAGAAACCATGTGTCAGATCCTCCCCA
        ------------+---------+---------+---------+---------+---------+   420
        AACTCGAAGAGTCTCTGTCGCTCATGCTCTGACGTCTTTGGTACACAGTCTAGGAGGGGT

50  E   L   L   R   D   S   E   Y   E   T   A   E   T   M   C   Q   I   L   P   K   49

421 AGGGGGTGGTCGCTGTCCTCGGACCATCGTCCAGCCCAGCCTCCAGCTCCATCATCAGCA
        ------------+---------+---------+---------+---------+---------+   480
        TCCCCCACCAGCGACAGGAGCCTGGTAGCAGGTCGGGTCGGAGGTCGAGGTAGTAGTCGT

```
     ACATCTGTGGAGAGAAGGAGGTCCCTCACTTCAAAGTGGCCCCAGAGGAGTTCGTCAAGT
481  ------------------------------------------------------------  540
     TGTAGACACCTCTCTTCCTCCAGGGAGTGAAGTTTCACCGGGGTCTCCTCAAGCAGTTCA

90   I  C  G  E  K  E  V  P  H  F  K  V  A  P  E  E  F  V  K  F  109

TCCAGTTCCAGAGATTCACAACCCTGAACCTCCACCCCAGCAACACTGACATCAGCGTGG
541  ------------------------------------------------------------  600
     AGGTCAAGGTCTCTAAGTGTTGGGACTTGGAGGTGGGGTCGTTGTGACTGTAGTCGCACC

110   Q  F  Q  R  F  T  T  L  N  L  H  P  S  N  T  D  I  S  V  A  129

BamHI        XmnI
     CTGTAGCTGGGATCCTGAACTTCTTCAACTGCACCACCGCCTGCCTCATCTGTGCCAAAG
601  ------------------------------------------------------------  660
     GACATCGACCCTAGGACTTGAAGAAGTTGACGTGGTGGCGGACGGAGTAGACACGGTTTC

130   V  A  G  I  L  N  F  F  N  C  T  T  A  C  L  I  C  A  K  A  149

CAGAATGCCTTTTAAACCTAGAGAAGCTGCTCCGGCAATTCCTTATCTCCAAGGACACGC
661  ------------------------------------------------------------  720
     GTCTTACGGAAAATTTGGATCTCTTCGACGAGGCCGTTAAGGAATAGAGGTTCCTGTGCG

150   E  C  L  L  N  L  E  K  L  L  R  Q  F  L  I  S  K  D  T  L  169

TGTCCGTCCGCATGCTGGATGACACCCGGGACCCCACCCCGCTCCTCAAGGAGATCCGGG
721  ------------------------------------------------------------  780
     ACAGGCAGGCGTACGACCTACTGTGGGCCCTGGGGTGGGGCGAGGAGTTCCTCTAGGCCC

170   S  V  R  M  L  D  D  T  R  D  P  T  P  L  L  K  E  I  R  D  189

ACGACAAGACCGCCACCATCATCATCCACGCCAACGCCTCCATGTCCCACACCATCCTCC
781  ------------------------------------------------------------  840
     TGCTGTTCTGGCGGTGGTAGTAGTAGGTGCGGTTGCGGAGGTACAGGGTGTGGTAGGAGG

190   D  K  T  A  T  I  I  I  H  A  N  A  S  M  S  H  T  I  L  L  209

TGAAGGCAGCCGAACTTGGGATGGTGTCAGCCTATTACACATACATCTTCACTAATCTGG
841  ------------------------------------------------------------  900
     ACTTCCGTCGGCTTGAACCCTACCACAGTCGGATAATGTGTATGTAGAAGTGATTAGACC

210   K  A  A  E  L  G  M  V  S  A  Y  Y  T  Y  I  F  T  N  L  E  229

AGTTCTCACTCCAGAGAACGGACAGCCTTGTGGATGATCGTGTCAACATCCTGGGATTTT
901  ------------------------------------------------------------  960
     TCAAGAGTGAGGTCTCTTGCCTGTCGGAACACCTACTAGCACAGTTGTAGGACCCTAAAA

230   F  S  L  Q  R  T  D  S  L  V  D  D  R  V  N  I  L  G  F  S  249

CCATTTTCAACCAATCCCATGCTTTCTTCCAAGAGTTTGCCCAGAGCCTCAACCAGTCCT
961  ------------------------------------------------------------  1020
     GGTAAAAGTTGGTTAGGGTACGAAAGAAGGTTCTCAAACGGGTCTCGGAGTTGGTCAGGA

```
1021  GGCAGGAGAACTGTGACCATGTGCCCTTCACTGGGCCTGCGCTCTCCTCGGCCCTGCTGT  1080
      CCGTCCTCTTGACACTGGTACACGGGAAGTGACCCGGACGCGAGAGGAGCCGGGACGACA
270    Q  E  N  C  D  H  V  P  F  T  G  P  A  L  S  S  A  L  L  F   289
                                   HphI

1081  TTGATGCTGTCTATGCTGTGGTGACTGCGGTGCAGGAACTGAACCGGAGCCAAGAGATCG  1140
      AACTACGACAGATACGACACCACTGACGCCACGTCCTTGACTTGGCCTCGGTTCTCTAGC
290    D  A  V  Y  A  V  V  T  A  V  Q  E  L  N  R  S  Q  E  I  G   309

1141  GCGTGAAGCCCTTGTCCTGCGGCTCGGCCCAGATCTGGCAGCACGGCACCAGCCTCATGA  1200
      CGCACTTCGGGAACAGGACGCCGAGCCGGGTCTAGACCGTCGTGCCGTGGTCGGAGTACT
310    V  K  P  L  S  C  G  S  A  Q  I  W  Q  H  G  T  S  L  M  N   329
                                                    EcoRI

1201  ACTACCTGCGCATGGTAGAATTGGAAGGTCTTACCGGCCACATTGAATTCAACAGCAAAG  1260
      TGATGGACGCGTACCATCTTAACCTTCCAGAATGGCCGGTGTAACTTAAGTTGTCGTTTC
330    Y  L  R  M  V  E  L  E  G  L  T  G  H  I  E  F  N  S  K  G   349

1261  GCCAGAGGTCCAACTACGCTTTGAAAATCTTACAGTTCACAAGGAATGGTTTTCGGCAGA  1320
      CGGTCTCCAGGTTGATGCGAAACTTTTAGAATGTCAAGTGTTCCTTACCAAAAGCCGTCT
350    Q  R  S  N  Y  A  L  K  I  L  Q  F  T  R  N  G  F  R  Q  I   369

1321  TCGGCCAGTGGCACGTGGCAGAGGGCCTCAGCATGGACAGCCACCTCTATGCCTCCAACA  1380
      AGCCGGTCACCGTGCACCGTCTCCCGGAGTCGTACCTGTCGGTGGAGATACGGAGGTTGT
370    G  Q  W  H  V  A  E  G  L  S  M  D  S  H  L  Y  A  S  N  I   389
                                   HphI

1381  TCTCGGACACTCTCTTCAACACCACCCTGGTCGTCACCACCATCCTGGAAAACCCATATT  1440
      AGAGCCTGTGAGAGAAGTTGTGGTGGGACCAGCAGTGGTGGTAGGACCTTTTGGGTATAA
390    S  D  T  L  F  N  T  T  L  V  V  T  T  I  L  E  N  P  Y  L   409

1441  TAATGCTGAAGGGGAACCACCAGGAGATGGAAGGCAATGACCGCTACGAGGGCTTCTGTG  1500
      ATTACGACTTCCCCTTGGTGGTCCTCTACCTTCCGTTACTGGCGATGCTCCCGAAGACAC
410    M  L  K  G  N  H  Q  E  M  E  G  N  D  R  Y  E  G  F  C  V   429

1501  TGGACATGCTCAAGGAGCTGGCAGAGATCCTCCGATTCAACTACAAGATCCGCCTGGTTG  1560
      ACCTGTACGAGTTCCTCGACCGTCTCTAGGAGGCTAAGTTGATGTTCTAGGCGGACCAAC
430    D  M  L  K  E  L  A  E  I  L  R  F  N  Y  K  I  R  L  V  G   449
```

FIG. 1(d)

```
1561 GGGATGGCGTGTACGGCGTTCCCGAGGCCAACGGCACCTGGACGGGAATGGTCGGGGAGC 1620
     CCCTACCGCACATGCCGCAAGGGCTCCGGTTGCCGTGGACCTGCCCTTACCAGCCCCTCG

450   D  G  V  Y  G  V  P  E  A  N  G  T  W  T  G  M  V  G  E  L  469
                                       HphI
1621 TGATCGCTAGGAAAGCAGATCTGGCTGTGGCAGGCCTCACCATTACAGCTGAACGGGAGA 1680
     ACTAGCGATCCTTTCGTCTAGACCGACACCGTCCGGAGTGGTAATGTCGACTTGCCCTCT

470   I  A  R  K  A  D  L  A  V  A  G  L  T  I  T  A  E  R  E  K  489
                     HphI
1681 AGGTGATTGATTTCTCTAAGCCATTCATGACTCTGGGAATTAGCATTCTTTACCGCATTC 1740
     TCCACTAACTAAAGAGATTCGGTAAGTACTGAGACCCTTAATCGTAAGAAATGGCGTAAG

490   V  I  D  F  S  K  P  F  M  T  L  G  I  S  I  L  Y  R  I  H  509

1741 ATATGGGACGCAAACCCGGCTATTTCTCCTTCCTGGACCCATTTTCTCCGGGCGTCTGGC 1800
     TATACCCTGCGTTTGGGCCGATAAAGAGGAAGGACCTGGGTAAAAGAGGCCCGCAGACCG

510   M  G  R  K  P  G  Y  F  S  F  L  D  P  F  S  P  G  V  W  L  529

1801 TCTTCATGCTTCTAGCCTATCTGGCCGTCAGCTGTGTCCTCTTCCTGGTGGCTCGGTTGA 1860
     AGAAGTACGAAGATCGGATAGACCGGCAGTCGACACAGGAGAAGGACCACCGAGCCAACT

530   F  M  L  L  A  Y  L  A  V  S  C  V  L  F  L  V  A  R  L  T  549

1861 CGCCCTACGAGTGGTACAGCCCACACCCATGTGCCCAGGGCCGGTGCAACCTCCTGGTGA 1920
     GCGGGATGCTCACCATGTCGGGTGTGGGTACACGGGTCCCGGCCACGTTGGAGGACCACT

550   P  Y  E  W  Y  S  P  H  P  C  A  Q  G  R  C  N  L  L  V  N  569
              HphI
1921 ACCAGTACTCCCTGGGCAACAGCCTCTGGTTTCCGGTCGGGGGGTTCATGCAGCAGGGCT 1980
     TGGTCATGAGGGACCCGTTGTCGGAGACCAAAGGCCAGCCCCCAAGTACGTCGTCCCGA

570   Q  Y  S  L  G  N  S  L  W  F  P  V  G  G  F  M  Q  Q  G  S  589

1981 CCACCATCGCCCCTCGCGCCTTATCCACCCGCTGTGTCAGTGGCGTCTGGTGGGCATTCA 2040
     GGTGGTAGCGGGGAGCGCGGAATAGGTGGGCGACACAGTCACCGCAGACCACCCGTAAGT

590   T  I  A  P  R  A  L  S  T  R  C  V  S  G  V  W  W  A  F  T  609

2041 CGCTGATCATCATCTCATCCTACACGGCCAACCTGGCAGCCTTCCTGACCGTGCAGCGCA 2100
     GCGACTAGTAGTAGAGTAGGATGTGCCGGTTGGACCGTCGGAAGGACTGGCACGTCGCGT

```
2101  TGGATGTGCCCATTGAGTCAGTGGATGACCTGGCTGACCAGACCGCCATTGAATATGGCA  2160
      ACCTACACGGGTAACTCAGTCACCTACTGGACCGACTGGTCTGGCGGTAACTTATACCGT

630   D  V  P  I  E  S  V  D  D  L  A  D  Q  T  A  I  E  Y  G  T  649

2161  CAATTCACGGAGGCTCCAGCATGACCTTCTTCCAAAATTCCCGCTACCAGACCTACCAAC  2220
      GTTAAGTGCCTCCGAGGTCGTACTGGAAGAAGGTTTTAAGGGCGATGGTCTGGATGGTTG

650   I  H  G  G  S  S  M  T  F  F  Q  N  S  R  Y  Q  T  Y  Q  R  669

2221  GCATGTGGAATTACATGTATTCCAAGCAGCCCAGCGTGTTCGTGAAGAGCACAGAGGAGG  2280
      CGTACACCTTAATGTACATAAGGTTCGTCGGGTCGCACAAGCACTTCTCGTGTCTCCTCC

670   M  W  N  Y  M  Y  S  K  Q  P  S  V  F  V  K  S  T  E  E  G  689

EcoRI
                    |
2281  GAATCGCCAGGGTGTTGAATTCCAACTACGCCTTCCTCCTGGAATCCACCATGAACGAGT  2340
      CTTAGCGGTCCCACAACTTAAGGTTGATGCGGAAGGAGGACCTTAGGTGGTACTTGCTCA

690   I  A  R  V  L  N  S  N  Y  A  F  L  L  E  S  T  M  N  E  Y  709

2341  ACTATCGGCAGCGAAACTGCAACCTCACTCAGATTGGGGGCCTGCTGGACACCAAGGGCT  2400
      TGATAGCCGTCGCTTTGACGTTGGAGTGAGTCTAACCCCCGGACGACCTGTGGTTCCCGA

710   Y  R  Q  R  N  C  N  L  T  Q  I  G  G  L  L  D  T  K  G  Y  729

2401  ATGGGATTGGCATGCCAGTCGGCTCGGTTTTCCGGGACGAGTTTGATCTGGCCATTCTCC  2460
      TACCCTAACCGTACGGTCAGCCGAGCCAAAAGGCCCTGCTCAAACTAGACCGGTAAGAGG

730   G  I  G  M  P  V  G  S  V  F  R  D  E  F  D  L  A  I  L  Q  749

PstI
                |
2461  AGCTGCAGGAGAACAACCGCCTGGAGATCCTGAAGCGCAAATGGTGGGAAGGAGGGAAGT  2520
      TCGACGTCCTCTTGTTGGCGGACCTCTAGGACTTCGCGTTTACCACCCTTCCTCCCTTCA

750   L  Q  E  N  N  R  L  E  I  L  K  R  K  W  W  E  G  G  K  C  769

SspI
                                               |
2521  GCCCCAAGGAGGAAGATCACAGAGCTAAAGGCCTGGGAATGGAGAATATTGGTGGAATCT  2580
      CGGGGTTCCTCCTTCTAGTGTCTCGATTTCCGGACCCTTACCTCTTATAACCACCTTAGA

770   P  K  E  E  D  H  R  A  K  G  L  G  M  E  N  I  G  G  I  F  789

2581  TTGTGGTTCTTATTTGTGGCTTAATCGTGGCCATTTTTATGGCTATGTTGGAGTTTTTAT  2640
      AACACCAAGAATAAACACCGAATTAGCACCGGTAAAAATACCGATACAACCTCAAAAATA

```
     GGACTCTCAGACACTCAGAAGCAACTGAGGTGTCCGTCTGCCAGGAGATGGTGACCGAGC
2641 ------------------------------------------------------------ 2700
     CCTGAGAGTCTGTGAGTCTTCGTTGACTCCACAGGCAGACGGTCCTCTACCACTGGCTCG

810  T  L  R  H  S  E  A  T  E  V  S  V  C  Q  E  M  V  T  E  L  829

HphI
             |
     TGCGCAGCATTATCCTGTGTCAGGACAGTATCCACCCCCGCCGGCGGCGCGCCGCAGTCC
2701 ------------------------------------------------------------ 2760
     ACGCGTCGTAATAGGACACAGTCCTGTCATAGGTGGGGGCGGCCGCCGCGCGGCGTCAGG

830  R  S  I  I  L  C  Q  D  S  I  H  P  R  R  R  R  A  A  V  P  849

CGCCGCCCCGGCCCCCCATCCCCGAGGAGCGCCGACCGCGGGGCACGGCGACGCTCAGCA
2761 ------------------------------------------------------------ 2820
     GCGGCGGGGCCGGGGGGTAGGGGCTCCTCGCGGCTGGCGCCCCGTGCCGCTGCGAGTCGT

850  P  P  R  P  P  I  P  E  E  R  R  P  R  G  T  A  T  L  S  N  869

ACGGGAAGCTGTGCGGGGCAGGGGAGCCCGACCAGCTCGCGCAGAGACTGGCGCAGGAGG
2821 ------------------------------------------------------------ 2880
     TGCCCTTCGACACGCCCCGTCCCCTCGGGCTGGTCGAGCGCGTCTCTGACCGCGTCCTCC

870  G  K  L  C  G  A  G  E  P  D  Q  L  A  Q  R  L  A  Q  E  A  889

CCGCCCTGGTGGCCCGCGGCTGCACGCACATCCGCGTCTGCCCCGAGTGCCGCCGCTTCC
2881 ------------------------------------------------------------ 2940
     GGCGGGACCACCGGGCGCCGACGTGCGTGTAGGCGCAGACGGGGCTCACGGCGGCGAAGG

890  A  L  V  A  R  G  C  T  H  I  R  V  C  P  E  C  R  R  F  Q  909

AGGGCCTGCGGGCACGGCCGTCGCCCGCCCGCAGCGAGGAGAGCCTGGAGTGGGAGAAAA
2941 ------------------------------------------------------------ 3000
     TCCCGGACGCCCGTGCCGGCAGCGGGCGGGCGTCGCTCCTCTCGGACCTCACCCTCTTTT

910  G  L  R  A  R  P  S  P  A  R  S  E  E  S  L  E  W  E  K  T  929

CCACCAACAGCAGCGAGCCCGAGTAGTCCCGGAGGCCACAGGACGCGCAGAGGCCGGGCG
3001 ------------------------------------------------------------ 3060
     GGTGGTTGTCGTCGCTCGGGCTCATCAGGGCCTCCGGTGTCCTGCGCGTCTCCGGCCCGC

930  T  N  S  S  E  P  E  936 *

Sal I              Bam H I
          |                    |
     GGGCGGGAGGGGAGGGGCGGGGCGGGCGCTGCTGTCAGCCGCCAGCCGGAACTTGTACAG
3061 ------------------------------------------------------------ 3120
     CCCGCCCTCCCCTCCCCGCCCCGCCCGCGACGACAGTCGGCGGTCGGCCTTGAACATGTC

CGTCGACACCTCTCCAGATTTCGGATCCAGTCACTTTTCAAAAAGATCAAGGAGCCTGAC
3121 ------------------------------------------------------------ 3180
     GCAGCTGTGGAGAGGTCTAAAGCCTAGGTCAGTGAAAAGTTTTTCTAGTTCCTCGGACTG

GCCCCAGCCAGAGACCGCGCCCGGTCAGGGAGCAGGGTCCACCCGGAAACGTTGCACCCA
3181 ------------------------------------------------------------ 3240
     CGGGGTCGGTCTCTGGCGCGGGCCAGTCCCTCGTCCCAGGTGGGCCTTTGCAACGTGGGT
```

FIG. I(g)

```
3241 AAGGGCAAAGGACGGCCCTCCCTCCTGGGCACAAGGACCCATCTTCTCCCAGTGGGTCTT 3300
     TTCCCGTTTCCTGCCGGGAGGGAGGTCCCGTGTTCCTGGGTAGAAGAGGGTCACCCAGAA

3301 TCCCTCTCGCCAAAATAACAAGAGTATAGGGTGGGGGGTCCCTACCCAGACCAGTCCAAT 3360
     AGGGAGAGCGGTTTTATTGTTCTCATATCCCACCCCCCAGGGATGGGTCTGGTCAGGTTA

3361 GAATTGGTGGAATCATCAGTTGAATTTTCCCCCTAGTCAGGGGCCAATGTACCCTCCGTCT 3420
     CTTAACCACCTTAGTAGTCAACTTAAAGGGGGATCAGTCCCCGGTTACATGGGAGGCAGA
                                                    Xmn I
                                                     |
3421 AGTTCTTACAGAAAAAAAAAAAAATTAAACAGGGAAGTTTTTCTTTTCTGGATTTGTATA 3480
     TCAAGAATGTCTTTTTTTTTTTTAATTTGTCCCTTCAAAAAGAAAAGACCTAAACATAT

3481 TTTTTGTTAATGTTCTTTTTCCCTTTTCTTTCCTCCTCTCCTTTTCTTCTTTGTCATCTTC 3540
     AAAAACAATTACAAGAAAAGGGAAAAGAAAGGAGGAGAGGAAAAGAAGAAACAGTAGAAG

3541 TCAGTCCTGTTAATTTGTTTTGTGTTTTTTGGAGGGGGAGGCTGGGTTAGGGAATGGAAG 3600
     AGTCAGGACAATTAAACAAAACACAAAAAACCTCCCCCTCCGACCCAATCCCTTACCTTC
                                                           SspI
                                                            |
3601 CCTAAATAATCCCTATTTCTTCTTTTTCCTGAATTTTGGAATATTGCGTTACCAGTGCAT 3660
     GGATTTATTAGGGATAAAGAAGAAAAAGGACTTAAAACCTTATAACGCAATGGTCACGTA
                                                      HphI  PstI
                                                        |    |
3661 CCGATTTCAGGTGCGGAACTCTCTGTATGGTGACTGAGGGGCCTGGAT 3708
     GGCTAAAGTCCACGCCTTGAGAGACATACCACTGACTCCCCGGACCTA
```

FIG.4(b)

COMPARISON OF SELECTED REGIONS OF HUMAN EAA1 FAMILY, SHOWING SPECIFIC INSERTION (i.e. HumEAA1d), DELETION (i.e. HumEAA1c) AND NUCLEOTIDE SUBSTITUTION (i.e. HumEAA1b) RELATIVE TO HumEAA1a

```
                                          GTTTTGCTGCA                                      1748
                                                                                            v
HUMAN EAA 1d    CGTCACCACCATCCT  ><  GGAAAAACCCATATTTAATGCTGAAGGGGAACCAC ------//------    GTT ---
                                                                                           Val 1737
                                                                                            v
HUMAN EAA 1a    CGTCACCACCATCCT  ><  GGAA AAACCCATATTTAATGCTGAAGGGGAACCAC ------//------    GTT ---
Nucleotide      ^                                                                          Val
                1412

1737
                                                                                            v
HUMAN EAA 1b    CGTCACCACCATCCT  ><  GGAAAAACCCATATTTAATGCTGAAGGGGAACCAC ------//------    ATT ---
                                                                                           Ile 1713
                                                                                            v
HUMAN EAA 1c    CGTCACCACCATCCT  ><  .................GGGGAACCAC ------//------            ATT ---
                                                                                           Ile
```

KAINATE-BINDING HUMAN CNS RECEPTORS OF THE EAA1 FAMILY

This application is a continuation of application Ser. No. 07/750,090, filed Aug. 26, 1991 now abandoned.

FIELD OF THE INVENTION

This invention is concerned with applications of recombinant DNA technology in the field of neurobiology. More particularly, the invention relates to the cloning and expression of DNA coding for excitatory amino acid (EAA) receptors, especially human EAA receptors.

BACKGROUND TO THE INVENTION

In the mammalian central nervous system (CNS), the transmission of nerve impulses is controlled by the interaction between a neurotransmitter substance released by the "sending" neuron and a surface receptor on the "receiving" neuron. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, and various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy-5-methyl-isoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

This family of glutamate-binding EAA receptors is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are generically engineered to produce only the receptor of interest. With cell lines expressing cloned receptor genes, a substrate which is homogeneous for the desired receptor is provided, for drug screening programs.

Very recently, genes encoding substituent polypeptides of EAA receptors from non-human sources, principally rat, have been discovered. Hollmann et al., Nature 342: 643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettler et al., Neuron 5: 583, 1990 described GluR5. Keinanen et al., supra, described genes called GluR-A, GluR-B, GluR-C and GluR-D which correspond precisely to GluR1, GluR2, GluR3 and GluR4 respectively. Sommer et al., Science 249: 1580, 1990 also showed, for GluR-A, GluR-B, GluR-C and GluR-D two alternatively spliced forms for each gene. These authors, as well as Monyer et al., Neuron 6: 799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et al., Science 252: 851, 1991; Verdoorn et al., Science 252: 1715, 1991; and see WO 91/06648).

Some recent work has also been published regarding non-human genes which appear to encode the kainate-type of receptor. Egebjerg et al., Nature 351: 745, 1991, have described the isolation of a gene from rat called GluR6, which although related in sequence to the AMPA receptor genes, forms a receptor which is not activated by AMPA but rather by glutamate, quisqualate, and preferentially, kainate. Other kainate-binding proteins have been described from frog (Wada et al., Nature 342: 684, 1989), chicken (Gregor et al., Nature 342: 689, 1989) and from rat (Werner et al., Nature 351: 742, 1991). These latter genes encode proteins which bind kainate, but which do not readily form into functional ion channels when expressed by themselves.

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al, supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly, are objects of the present invention.

It is another object of the present invention to provide in isolated form a DNA molecule which codes for a human EAA receptor.

It is another object of the present invention to provide a cell that has been genetically engineered to produce a kainate-binding human EAA receptor.

Other objects of the present invention will be apparent from the following description of the invention.

SUMMARY OF THE INVENTION

Genes coding for a family of EAA receptors endogenous to human brain have now been identified and characterized. A representative member of this human EAA receptor family, designated human EAA1a, codes for a receptor protein that in addition to binding glutamate with an affinity typical of EAA receptors, also exhibits ligand binding properties characteristic of kainate-type EAA receptors. Sequence-related genes coding for naturally occurring variants of the human EAA1a receptor have also been identified, and constitute additional members of this receptor family, herein referred to as the human EAA1 receptor family.

The present invention thus provides, in one of its aspects, an isolated polynucleotide, consisting either of DNA or of RNA, which codes for a human EAA1 receptor or for a kainate-binding fragment thereof.

In another aspect of the present invention, there is provided a cell that has been genetically engineered to produce a kainate-binding, human EAA receptor belonging to the herein-defined EAA1 family. In related aspects of the present invention, there are provided recombinant DNA constructs and relevant methods useful to create such cells.

In another aspect of the present invention, there is provided a method for evaluating the the affinity of a selected compound for binding to a receptor having the characteristics of a human EAA1 receptor, which comprises the steps of incubating the compound with a genetically engineered cell of the present invention, or with a membrane preparation derived therefrom, in a manner suitable to determine the receptor binding affinity of the test compound.

Other aspects of the present invention, which encompass various applications of the discoveries herein described, will become apparent from the following detailed description, and from the accompanying drawings.

BRIEF REFERENCE TO THE DRAWINGS

FIGS. 1(a) to 1(g) provide the nucleotide sequence (SEQ ID NO:1) of DNA coding for an excitatory amino acid receptor of the present invention, and the deduced amino acid sequence (SEQ ID NO:2) thereof;

FIG. 2 illustrates schematically a PCR-based strategy for amplifying the DNA sequence illustrated in FIGS. 1(a)–1(g) (Primers 1–8 are shown in SEQ ID NOS. 3–10, respectively);

FIGS. 3(a), 3(b) and 3(c) illustrate with linear plasmid maps the strategy used to construct expression vectors harbouring the DNA sequence illustrated in FIGS. 1(a)–1(g) (The sequences shown in FIG. 3(b) are also disclosed in SEQ ID NOS. 11 and 12);

FIGS. 4(a) and 4(b) (SEQ ID NOS. 13–15) show, with reference to FIGS. 1(a)–1(g), the DNA and amino acid sequences of naturally occurring variants of the EAA receptor illustrated in FIG. 1(a)–1(g); and FIG. 5 illustrates graphically the ligand-binding properties of the EAA receptor expressed from the coding region provided in FIGS. 1(a)–1(g).

DETAILED DESCRIPTION OF THE INVENTION AND ITS PREFERRED EMBODIMENTS

Figure 2:
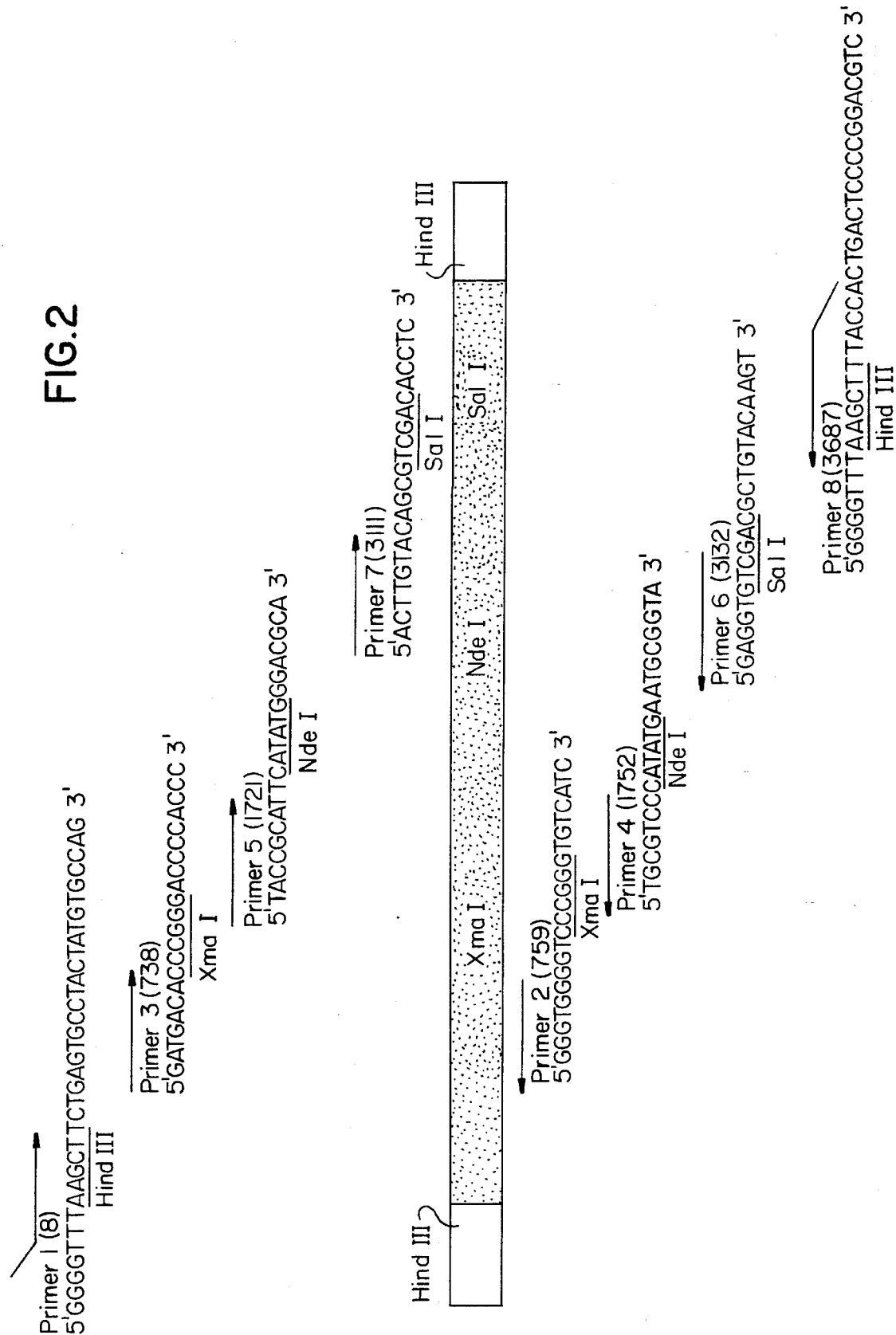

The invention relates to excitatory amino acid (EAA) receptors of human origin, and is directed more particularly to a novel family of kainate-type human EAA receptors, herein designated the human EAA1 receptor family. As used herein, the term "human EAA1 receptor" is intended to embrace the human EAA1a receptor, and kainate-binding variants of the EAA1a receptor that are structurally related thereto, i.e., have at least 95% homology therewith, including naturally occurring and synthetically derived variants of the EAA1a receptor. Naturally occurring variants of the human EAA1a receptor include particularly the receptors herein designated human EAA1b receptor, human EAA1c receptor and human EAA1d receptor. As used herein, the term "kainate-binding" refers to receptor variants and receptor fragments that display greater binding affinity for kainate than for either glutamate, AMPA or NMDA, as determined in assays of conventional design, such as the assays herein described.

Each of the naturally occurring members of the EAA1 family possesses structural features characteristic of the EAA receptors in general, including extracellular N- and C-terminal regions, as well as four internal hydrophobic domains which serve to anchor the receptor within the cell surface membrane. The particular human EAA receptor designated EAA1 a is a protein characterized structurally as a single polypeptide chain that is produced initially in precursor form bearing an 20 residue N-terminal signal peptide, and is transported to the cell surface in mature form, lacking the signal peptide and consisting of 936 amino acids arranged in the sequence illustrated, by single letter code, in FIGS. 1(a)–1(g). Unless otherwise stated, amino acid residues of the EAA1 receptors are numbered with reference to the mature protein sequence. With respect to structural domains of the receptor, hydropathy analysis reveals four putative transmembrane domains, one spanning residues 527–546 inclusive (TM-1), another spanning residues 571–589 (TM-2), a third spanning residues 600–618 (TM-3) and the fourth spanning residues 785–805 (TM-4). Based on this assignment, it is likely that the human EAA1a receptor structure, in its natural membrane-bound form, consists of a 526 amino acid N-terminal extracellular domain, followed by a hydrophobic region containing four transmembrane domains and an extracellular, 131 amino acid C-terminal domain.

As shown in FIG. 4, structurally related variants of the EAA1a receptor, which occur naturally in human brain tissue, have also been identified. As deduced from nucleotide sequences of the genes coding for them, these variants share at least about 98% amino acid homology with EAA1a, i.e., have at least about 98% identity at the amino acid level, with respect to EAA1a. One variant, designated EAA1b, is virtually identical to EAA1a except for a single nucleotide difference, which results in a GTT to ATT codon substitution, and a valine to isoleucine change at the amino acid level. The two other variants, designated EAA1c and EAA1d, incorporate more substantial variations relative to EAA1a. The variant EAA1c is characterized by a 24 base pair deletion which results, at the amino acid level, in an eight residue deletion from an extracellular domain of the EAA1a receptor. The variant EAA1d, on the other hand, is characterized by an 11 nucleotide insertion at precisely the location where the 24 nucleotide deletion occurs in EAA1c. The 11 base pair insertion contained in EAA1d has the effect of shifting the reading frame, and in fact introduces stop condons at a location 3' of and neighbouring the insertion. As a result, the EAA1d-encoding DNA in fact encodes a truncated protein or, in essence, an extracellular fragment of EAA1a.

In human hippocampal cDNA libraries, the source from which DNA coding for the EAA1a receptor was isolated the EAA1a receptor is encoded by the nucleotide sequence provided in FIGS. 1(a)–1(g). Relative to EAA receptors previously discovered in rat tissue, as described in the publications mentioned hereinabove, members of the human EAA1 receptor family share not more than about 45% amino acid identity with such rat receptors, with the exception of the rat KA-1 protein described very recently by Werner et al, 1991, supra, which shares about 94% amino acid homology (identity) with human EAA1a. The human EAA1 receptors differ most significantly from this rat receptor in the extracellular, C-terminal region of the receptors.

Like other members of the human EAA1 receptor family, receptor family, receptor subtype EAA1a is characterized by a pharmacological profile i.e. a ligand binding "signature", that points strongly to a kainate-type pharmacology, as distinct from other excitatory amino acid receptor types, such as NMDA and AMPA. Despite the understanding that kainate binding receptors require a multi- and perhaps heteromeric subunit structure to function in the pharmacological sense, it has been found that cells producing the unitary EAA1a receptor do, independently of association with other receptor subunits, provide a reliable indication of excitatory amino acid binding. Thus, in a key aspect of the present invention, the human EAA1a receptor is exploited for the purpose of screening candidate compounds for the ability to compete with endogenous EAA receptor ligands and known synthetic analogues thereof, for EAA receptor binding.

For use in receptor binding assays, it is desirable to construct by application of genetic engineering techniques a mammalian cell that produces a human EAA1 receptor in functional form as a heterologous product. The construction of such cell lines is achieved by introducing into a selected host cell a recombinant DNA construct in which DNA coding for the human EAA1 receptor in a form transportable to the cell surface i.e., bearing its native signal peptide or a functional, heterologous equivalent thereof, is associated with expression controlling elements that are functional in the selected host to drive expression of the receptor-encoding DNA, and thus elaborate the desired EAA1 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human EAA1 receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevertheless serve as expression hosts, provided that "background" binding to the test ligand is accounted for in the assay results.

According to one embodiment of the present invention, the cell line selected to serve as host for EAA1 receptor production is a mammalian cell. Several types of such cell lines are currently available for genetic engineering work, and these include the chinese hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with these hosts and are now commercially available, and any one of these systems can be selected to drive expression of the EAA1 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for the transportable receptor precursor is linked with expression controlling DNA sequences recognized by the host, and which include a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as E. coli. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals, i.e., the metalothionein gene promoter, and other steroid-inducible promoters.

For incorporation into the recombinant DNA expression vector, DNA coding for the desired EAA1 receptor, i.e., the EAA1a receptor or a kainate-binding variant thereof, can be obtained by applying selected techniques of gene isolation or gene synthesis. As described in more detail in the examples herein, the EAA1a receptor, and the EAA1b, EAA1c and EAA1d variants thereof, are encoded within the genome of human brain tissue, and can therefore be obtained by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in for example a bacterial plasmid, more typically a bacteriophage. Such bacteriophage harbouring fragments of the human DNA are typically grown by plating on a lawn of susceptible $E.\ coli$ bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmidic vector for nucleic acid sequence analysis.

Having herein provided the nucleotide sequence of various human EAA1 receptors, it will be appreciated that automated techniques of gene synthesis and/or amplification can be performed to generate DNA coding therefor. Because of the length of the EAA1 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA1 gene family. It will be appreciated, for example, that polynucleotides coding for the EAA1 receptors herein described can be generated by substituting synonymous codons for those represented in the naturally occurring polynucleotide sequences herein identified. In addition, polynucleotides coding for synthetic variants of the EAA1 receptors herein described can be generated which for example incorporate one or more single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity, e.g., within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the $E.\ coli$ gpt gene which confers resistance to mycophenolic acid, the neo gene from transposon Tn5 which confers resistance to the antibiotic G418 and to neomycin, the dhfr sequence from murine cells or $E.\ coli$ which changes the phenotype of DHFR– cells into DHFR+ cells, and the tk gene of herpes simplex virus, which makes TK– cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e., ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells, can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human EAA1 receptor of the invention is evaluated typically using a predetermined amount of cell-derived membrane (measured for example by protein determination), generally from about 25 µg to 100 µg. Generally, competitive binding assays will be useful to evaluate the affinity of a test compound relative to kainate. This competitive binding assay can be performed by incubating the membrane preparation with radiolabelled kainate, for example [3H]-kainate, in the presence of unlabelled test compound added at varying concentrations. Following incubation, either displaced or bound radiolabelled kainate can be recovered and measured, to determine the relative binding affinities of the test compound and kainate for the particular receptor used as substrate. In this way, the affinities of various compounds for the kainate-type human EAA receptors can be measured.

As an alternative to using cells that express receptor-encoding DNA, ligand characterization may also be performed using cells, for example Xenopus oocytes, that yield functional membrane-bound receptor following introduction of messenger RNA coding for the EAA1 receptor. In this case, the EAA1 receptor gene of the invention is typically subcloned into a plasmidic vector such that the introduced gene may be easily transcribed into RNA via an adjacent RNA transcription promoter supplied by the plasmidic vector, for example the T3 or T7 bacteriphage promoters. RNA is then transcribed from the inserted gene in vitro, and can then be injected into Xenopus oocytes. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell.

In addition to using the receptor-encoding DNA to construct cell lines useful for ligand screening, expression of the DNA can, according to another aspect of the invention, be performed to produce fragments of the receptor in soluble form, for structure investigation, to raise antibodies and for other experimental uses. It is expected that the portion of the EAA1 receptor responsible for binding a ligand molecule resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length EAA1 receptor-encoding DNA may be modified by site-directed mutagenesis, so as to introduce a translational stop codon into the extracellular N-terminal region, immediately before the sequence encoding the first transmembrane domain (TM1), i.e., before residue 527 as shown in FIG. 1. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxy-terminus instead, for example domains immediately following the fourth transmembrane domain (TM4), i.e., residing between amino acid residues 805 and 936 inclusive of FIGS. 1(a)-1(g). In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly, or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promoter capable of high-level expression, for example the CMV (cytomegalovirus) promoter. Alternately, non-mammalian cells, such as insect Sf9 (*Spodoptera frugiperda*) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. Aspergillus nidulans, for example, with the expression being driven by the alcA promoter, would constitute such as acceptable system. In addition to such expression hosts, it will be further appreciated that any prokaryotic or other eukaryotic expression system capable of expressing heterologous genes or gene fragments, whether intracellularly or extracellularly would be similarly acceptable.

The availability of isolated extracellular ligand-binding domains of the receptor protein makes it feasible to determine the 3-dimensional structures of these ligand-binding regions, with or without a candidate ligand complexed thereto, by a combination of X-ray crystallographic and advanced 2D-NMR techniques. In this way, additional new candidate compounds, predicated to have the required interactions with the 3-dimensional receptor structure, can be specifically designed and tested.

With large domains, crystallography is the method of choice for structure determination of both the domain in isolation, and of the co-complex with the natural ligand (or an appropriate antagonist or agonist molecule). If a particular domain can be made small enough, for example approximately 100–130 amino acids in length, then the powerful technique of 2-D NMR can also be applied to structure determination. This enables not only the determination of the domain structure, but also provides dynamic information about the drug-receptor interaction.

For use particularly in detecting the presence and/or location of an EAA1 receptor, for example in brain tissue, the present invention also provides, in another of its aspects, labelled antibody to a human EAA1 receptor. To raise such antibodies, there may be used as immunogen either the intact, soluble receptor or an immunogenic fragment thereof, produced in a microbial or mammalian cell host as described above or by standard peptide synthesis techniques. Regions of the EAA1a receptor particularly suitable for use as immunogenic fragments include those corresponding in sequence to an extracellular region of the receptor, or a portion of the extracellular region, such as peptides consisting of residues 1–526, including particularly residues 106–120 or 178–191 or 463–509, and peptides corresponding to the region between transmembrane domains TM-2 and TM-3, such as a peptide consisting of residues 590–599. Peptides consisting of the C-terminal domain (residues 806–936), or fragment thereof such as a peptide consisting of residues 895–936 or 915–930, may also be used for the raising of antibodies. Substantially the same regions of the human EAA1b, EAA1c and EAA1d receptors may also be used for production of antibodies against these receptors.

The raising of antibodies to the desired EAA1 receptor or immunogenic fragment can be achieved, for polyclonal antibody production, using immunization protocols of conventional design, and any of a variety of mammalian hosts, such as sheep, goats and rabbits. Alternatively, for monoclonal antibody production, immunocytes such as splenocytes can be recovered from the immunized animal and fused, using hybridoma technology, to a myeloma cells. The fusion products are then screened by culturing in a selection medium, and cells producing antibody are recovered for continuous growth, and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for the human EAA1 receptor, and selected regions thereof, may also be used, in accordance with another aspect of the present invention, as hybridization probes, for example to identify sequence-related genes resident in the human or other mammalian genomes (or cDNA libraries) or to locate the EAA1-encoding DNA in a specimen, such as brain tissue. This can be done using either the intact coding region, or a fragment thereof having radiolabelled, e.g. $^{32}P$, nucleotides incorporated therein. To identify the EAA1-encoding DNA in a specimen, it is desirable to use either the full length cDNA coding therefor, or a fragment which is unique thereto. With reference to FIG. 1 and the nucleotide numbering appearing thereon, such nucleotide fragments include those corresponding in sequence to a region coding for the N-terminus or C-terminus of the receptor, or representing a 5'-untranslated or 3'-untranslated region thereof, such as one of the following nucleotide regions: 8–156, 157–1563, 531–575, 1278–1359, 2826–2909, 2958–3073 and 3024–3708. These sequences, and the intact gene itself, may also be used of course to clone EAA1-related human genes, particularly cDNA equivalents thereof, by standard hybridization techniques.

EXAMPLE 1

Isolation of DNA coding for the human EAA1a receptor

As a first step in the isolation of DNA coding for a human EAA receptor, the published nucleotide sequences of rat GluR1 receptor, and chicken and frog kainate binding proteins were compared to identify spaced regions of homology, capable of serving as sites for primer binding, and PCR-based amplification. Oligonucleotide primers putatively capable of hybridizing with sequence-related regions in human cDNA, and having non-hybridizing flanks bearing HindIII restriction sites for subsequent cloning work, were then synthesized based on the published sequence of the rat GluR1 gene using conventional technique of gene synthesis, to generate primers of the following sequence:
(SEQ ID NO:16) 5' GGGGTTTAAGCTTGAGCGTCCTCTTCCTGGT 3'
(SEQ ID NO:17) 5' GGGGTTTAAGCTTGTGAAGAACCACCAGACGCCG 3'

Using human hippocampal cDNA as template (obtained as an EcoRI-based lambda gt10 library from Clontech Laboratories (Palo Alto, Calif., U.S.A.) the primers were then used in an attempt to amplify homologous sequences in the human cDNA, by application of the polymerase chain reaction technique. Reaction mixtures contained in 100M, 100 ng of human hippocampal cDNA, 125 pmol of each primer and 2U Taq polymerase (in 10 mM Tris-HCl, pH9.0, 50 mM KCl, 1.5 mM $MgCl_2$, and with 0.2 mM of each deoxyribonucleotide species). There were then performed thirty cycles of 94C/1 min; 58C/1 min; 72C/2 min, followed by a final cycle of 72C/30 min.

There was generated an amplification product having an expected nucleotide length (239bp). The product of amplification was then liberated from the gel and sub-cloned for sequencing into the HindIII site of phagemid vector pTZ19 (Pharmacia). The nucleotide sequence of the amplification product (without primers) is represented, retrospectively, from nucleotide #1850 to nucleotide #2020 inclusive (FIGS. 1(a)–1(g)). A comparison of the sequence amplified from the human cDNA template with the corresponding region of the rat GluR gene on which the oligonucleotide primers were based revealed only about 60% identity, indicating that a fragment from an unrelated human gene had been identified.

To isolate cDNA coding for the entire human EAA1a receptor, a lambda gt10-based library of human hippocampal cDNA was probed using a PCR-generated, labelled (alpha-$^{32}P$-dCTP) version of the 239bp amplification product. Of $10^6$ clones screened, probing identified 60 putative clones under the following high stringency hybridization conditions: 6×SSC, 50% formamide, 5% Denhardt's solution, 0.5% SDS, 100 μg/ml denatured salmon sperm DNA. Hybridizations were carried out at 37C overnight, and filters were washed with 2×SSC containing 0.5% SDS at 25C for 5 minutes, followed by a 15 minute wash at 50C with 2×SSC containing 0.5% SDS. The final wash was with 1×SSC containing 0.5% SDS at 50C for 15 minutes. Filters were exposed to X-ray film (Kodak) overnight.

Hybridization studies were performed in duplicate, and only those clones which hybridized well in both duplicates were selected for further analysis. Upon second round screening, 50 of the original 60 putative clones were selected. All 50 putative clones were plaque-purified, large scale DNA preps were made, and then DNA inserts liberated therefrom were subcloned into the EcoRI site of pTZ18 vectors, for sequence analysis. Sequencing revealed one clone harbouring, internally, a region with a nucleotide sequence identical to the sequence of the original 239bp subclone. The entire sequence of the isolated clone (1058bp) was then determined. Retrospectively, this 1058bp subclone is represented from nucleotide 1245 to nucleotide 2302 inclusive (FIGS. 1(a)–1(g)).

Figure 3A:
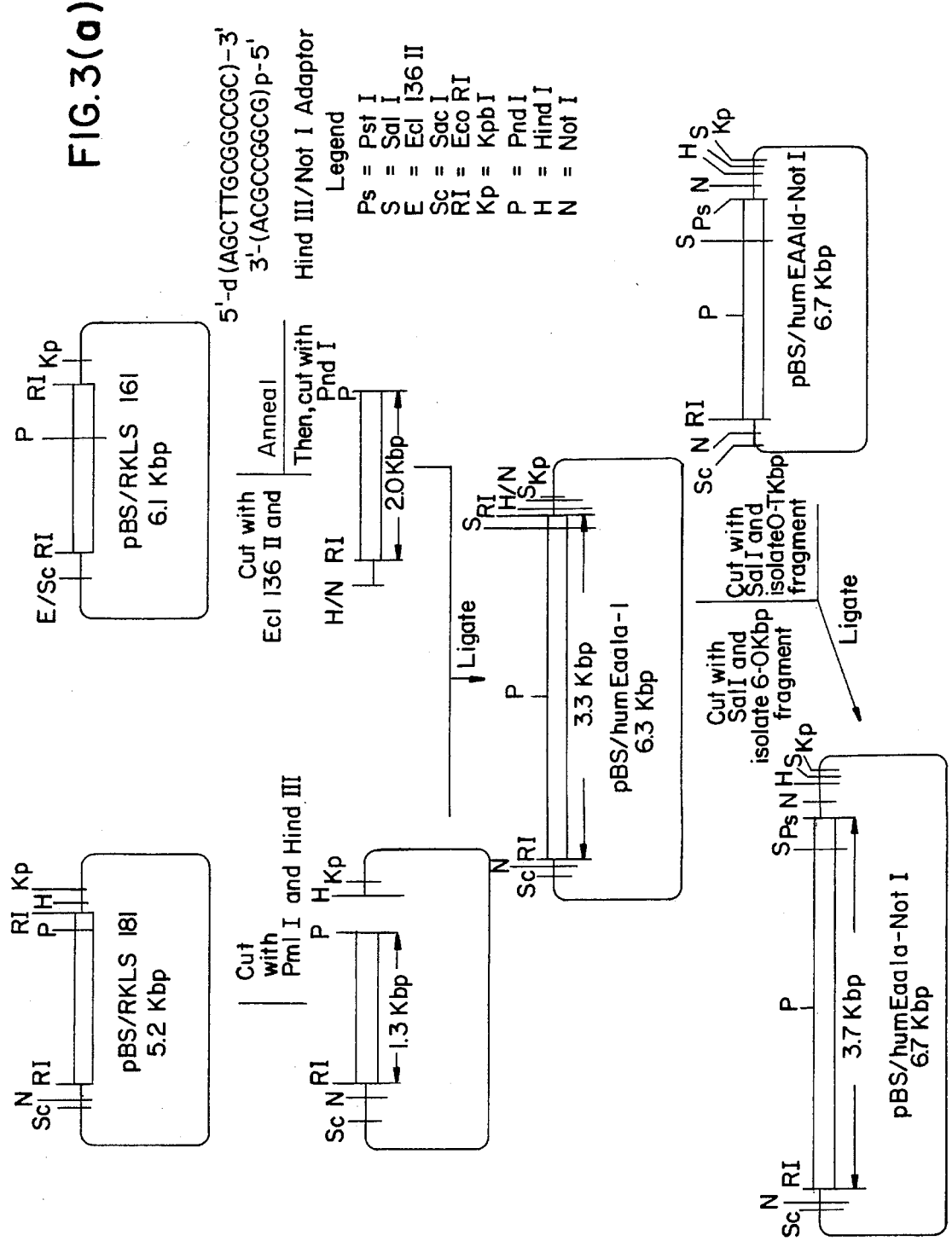
Figure 3B:
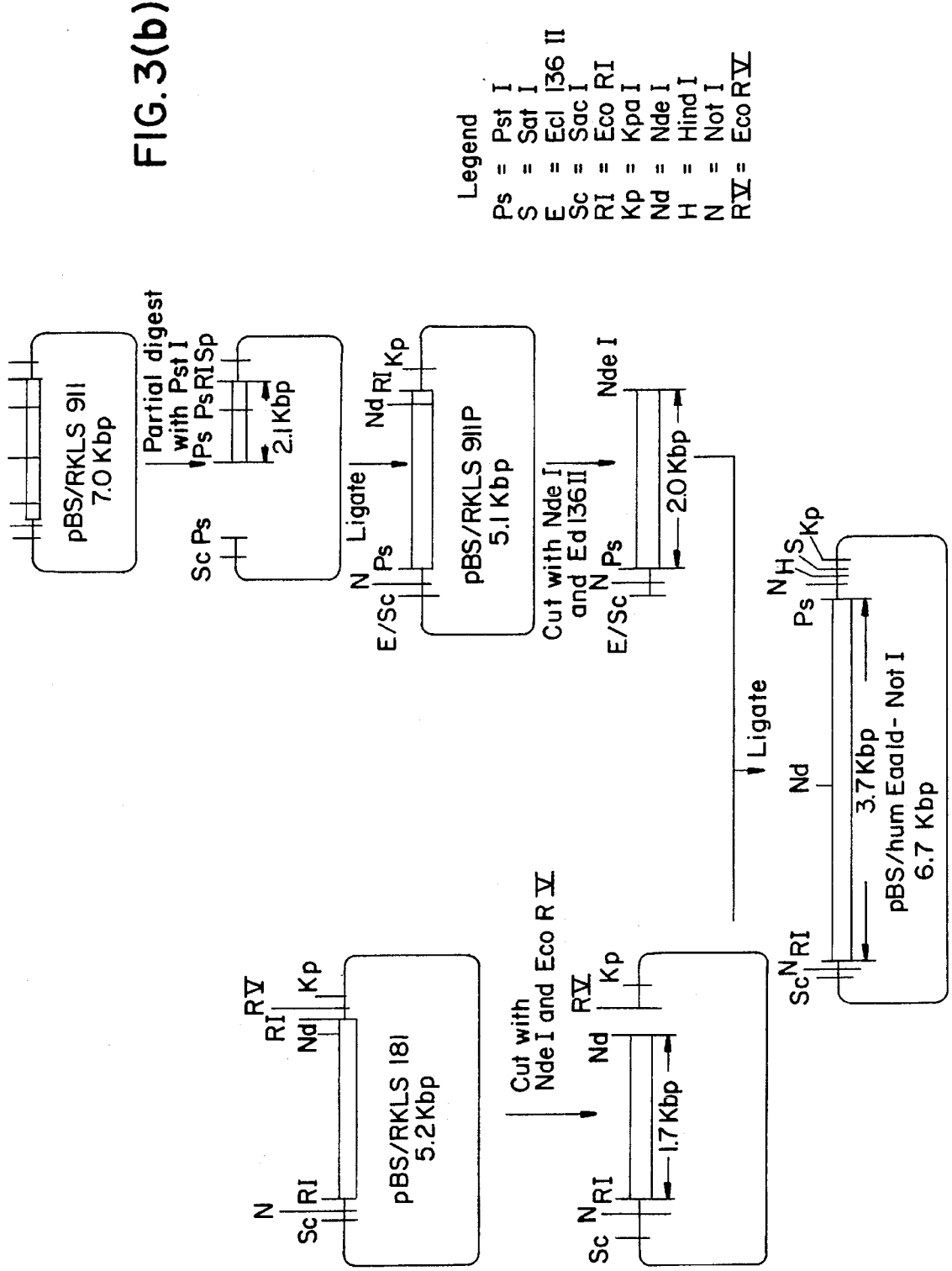
Figure 3C:
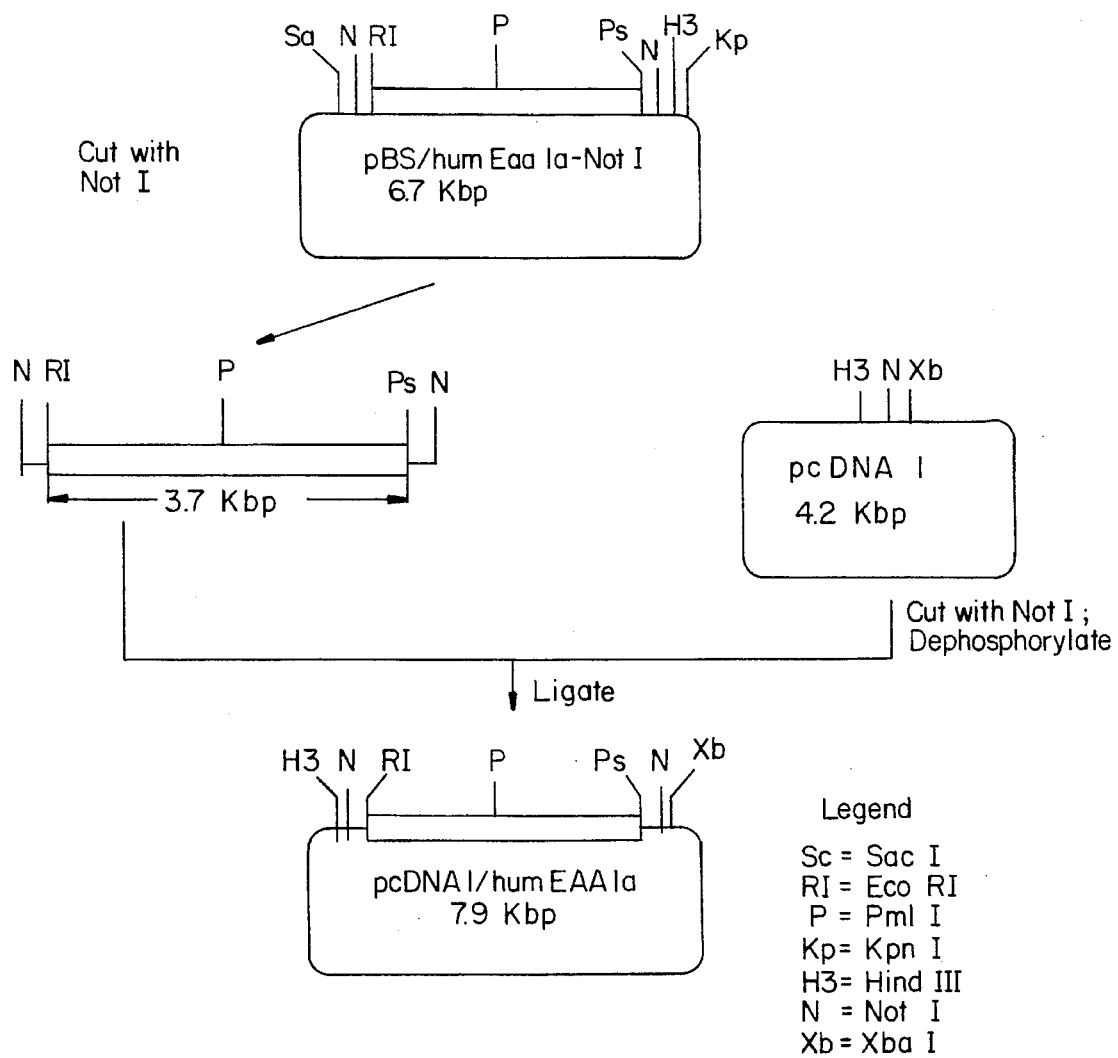

Since it was likely by analogy with the other receptor genes that the 1058bp was not full length, an alternative human hippocampal cDNA library constructed in a lambda phage system known commercially as lambda ZAP II was obtained (Stratagene Cloning Systems, La Jolla, Calif., U.S.A.) and screened using a PCR-generated, radiolabelled version of the 1058bp sub-clone. Screening of $10^6$ clones of this library by hybridization under the stringency conditions detailed above lead initially to the selection of 50 positive clones. For sequencing, phagemids carrying the inserts were excised, to generate insert-carrying variants of the phagemid vector known commercially as Bluescript-SK. Sequencing analysis identified two phagemid clones sharing a sequence overlap. One clone carrying a 2.2kp EcoRI/EcoRI insert, and apparently representing a 5' region of the open reading frame, was designated pBS/RKLS181. The overlapping clone carrying a 3.1kp EcoRI/EcoRI insert and appearing to represent the remaining 3' region of the open reading frame, was designated pBS/RKLS161. To construct the entire open reading frame, the strategy shown in FIG. 3(1) was employed, to generate the phagemid pBS/HumEAA1a which carries the EAA1a-encoding DNA as a 3.7kb EcoRI/PstI insert (recoverable intact as a 3.7kb NotI/NotI insert) in a 3.0kb Bluescript-SK phagemid background. The entire sequence of the EcoRI/PstI insert is provided in FIGS. 1(a)–1(g).

The 6.7kb phagemid pBS/humEAA1a-NotI was deposited, under the terms of the Budapest Treaty, with the American Type Culture Collection in Rockville, Md. USA on Aug. 21, 1991, and has been assigned accession number ATCC 75063.

EXAMPLE 2

Alternative strategy for obtaining EAA1a receptor-encoding DNA

Having herein provided the nucleotide sequence of EAA1a-encoding DNA, it will be appreciated that isolation thereof by the procedures just described is unnecessary, and can be replaced by application of automated techniques of gene synthesis and amplification. Using an appropriate cDNA library as template, for example a carefully prepared human hippocampal cDNA library, the polymerase chain reaction technique can be applied to amplify the desired cDNA product. While current PCR protocols are unlikely to enable direct amplification of the entire 3.7kb gene, regional amplification to generate ligatable gene fragments is a feasible approach to gene construction.

With reference specifically to the EAA1a-encoding DNA, PCR-facilitated gene construction can proceed, for example, as illustrated in FIG. 2. More particularly, regions of the cloned cDNA template are amplified as fragments comprising on the order of several hundred nucleotides, using primers bearing non-hybridizing 5' flanks that constitute restriction sites useful in subsequent steps of gene assembly. In the example illustrated in FIG. 2, the gene is amplified as 4 individual fragments that can be ligated, because of the careful selection of restriction sites, in one step to form the entire EAA1 a receptor-encoding DNA.

It will also be appreciated that automated techniques of gene synthesis can be applied, to provide gene fragments that by PCR can be amplified and subsequently ligated. Using current protocols, for example as described by Barnett et al in Nucl. Acids Res., 1990, 18(10):3094, fragments up to about 300 bases in length can be synthesized, and then amplified again using restriction site-tailed primers to facilitate assembly of the de novo synthesized gene regions.

EXAMPLE 3

Construction of genetically engineered cells producing the human EAA1a receptor For transient expression in mammalian cells, cDNA coding for the human EAA1a receptor was incorporated into the mammalian expression vector pcDNA1, which is available commercially from Invitrogen Corporation (San Diego, Calif., USA; catalogue number V490-20). This is a multifunctional 4.2kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

For incorporation of the EAA1a receptor-encoding cDNA into an expression vector, the cDNA source insert was released from pBS/hum EAA1a-NotI as a 3.7kb NotI/NotI fragment, which was then incorporated at the NotI site in the pcDNAI polylinker. Sequencing across the NotI junction was performed, to confirm proper insert orientation in pcDNA1. The resulting plasmid, designated pcDNA1/humEAA1a, was then introduced for transient expression into a selected mammalian cell host, in this case the monkey-derived, fibroblast like cells of the COS-1 lineage (available from the American Type Culture Collection, Rockville, Md. as ATCC CRL 1650).

For transient expression of the EAA1-encoding DNA, COS-1 cells were transfected with approximately 8 µg DNA (as pcDNA1/humEAA1a) per $10^6$ COS cells, by DEAE-mediated DNA transfection and treated with chloroquine according to the procedures described by Maniatis et al, supra. Briefly, COS-1 cells were plated at a density of $5\times10^6$ cells/dish and then grown for 24 hours in FBS-supplemented DMEM/F12 medium. Medium was then removed and cells were washed in PBS and then in medium. There was then applied on the cells 10 ml of a transfection solution containing DEAE dextran (0.4 mg/ml), 100 uM chloroquine, 10% NuSerum, DNA (0.4 mg/ml) in DMEM/F12 medium. After incubation for 3 hours at 37C, cells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines were also prepared using two different cell types as host: CHO K1 and CHO Pro5. To construct these cell lines, cDNA coding for human EAA1a was incorporated into the NotI site of a 7.1kb derivative of plasmid vector pcDNA1, which incorporates the neomycin gene under control of the Rous Sarcoma Virus LTR promoter and is designated pcDNA1/NEO (available also from Invitrogen Corporation, catalogue #V492-20). In a similar fashion, and again using a convenient NotI site for insertion, the receptor-encoding cDNA was inserted into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells were first seeded at a density of $5\times10^5$ in 10% FBS-supplemented MEM medium. After growth for 24 hours, fresh medium was added to the plates and three hours later, the cells were transfected using the calcium phosphate-DNA co-precipitation procedure (Maniatis et al, supra). Briefly, 3 µg of DNA was mixed and incubated with buffered calcium solution for 10 minutes at room temperature. An equal volume of buffered phosphate solution was added and the suspension was incubated for 15 minutes at room temperature. Next, the incubated suspension was applied to the cells for 4 hours, removed and cells were shocked with medium containing 15% glycerol. Three minutes later, cells were washed with medium and incubated for 24 hours at normal growth conditions. Cells resistant to neomycin were selected in 10% FBS-supplemented alpha-MEM medium containing G418 (1 mg/ml). Individual colonies of G418-resistant cells were isolated about 2–3 weeks later, clonally selected and then propogated for assay purposes.

EXAMPLE 4

Ligand binding assays

Transfected cells in the frozen state were suspended in ice-cold distilled water using a hand homogenizer and centrifuged for 20 minutes at 50,000 g. The supernatant was discarded and the membrane pellet stored frozen at −70° C.

COS cell membrane pellets were suspended in ice cold 50 mM Tris-HCl (pH 7.55, 5° C.) and placed inside Spectrapor 7 (EDTA-treated, sulfur-free) dialysis tubing. The suspension was placed in 4 litres of ice cold 50 mM Tris-HCl (pH 7.55, 5° C.) and dialyzed for 16–24 hours at 5° C. in order to remove endogenous glutamate that would compete for binding. The tissue suspension was recovered from the tubing along with a small volume of buffer used to rinse the tubing. This resultant membrane preparation was used as tissue source for binding experiments described below. Proteins were determined using the Pierce Reagent with BSA as standard.

Binding assays were then performed, using an amount of COS-derived membrane equivalent to from 25–100 ng/ml as judged by protein determination and selected radiolabelled ligand. In particular, glutamate binding assays entailed formation of an incubation mixture consisting of 25–100 ug/ml of tissue protein, and [3,4-3H]L-glutamic acid (47.3 Ci/mmole, 10 mM final) in 50 mM Tris-HCl (pH 7.55, 5° C.) in 1 ml final volume. Non-specific binding was in the presence of 1 mM L-glutamate. Samples were incubated on ice for 60 minutes in plastic minivials. Bound and free ligand were separated by centrifugation for 10 minutes at 50,000 g (4° C.). Tissue pellets were washed superficially with 2×6 ml of ice cold incubation buffer. Pellets were solubilized and counted in 5 ml of Beckman Ready Protein Scintillation cocktail.

For kainate binding assays, incubation mixtures consisted of 25–100 ug/ml tissue protein and [vinylidene-3H] kainic acid (58Ci/mmole, 5 nM final) in the cold incubation buffer, 1 ml final volume. Non-specific binding was in the presence of 1 mM L-glutamate. Samples were incubated as for the glutamate binding assays, and bound and free ligand were separated by rapid filtration using a Brandel cell harvester and GF/B filters pre-soaked in ice-cold 0.3% polyethyleneimine. Filters were washed twice in 6 ml of the cold incubation buffer, then placed in scintillation vials with 5 ml of Beckman Ready-Safe scintillation cocktail for counting.

AMPA-binding assays were also performed in substantially the same manner described above for kainate binding, but using as ligand D,L-alpha-[5-methyl-3H]amino-3-hydroxy-5-methylisoxazole-4-propionic acid (3H-AMPA, 27.6Ci/mmole, 5 nM final) with 0.1M KSCN and 2.5 mM CaCl$_2$ in the 1 ml final volume.

Figure 5:
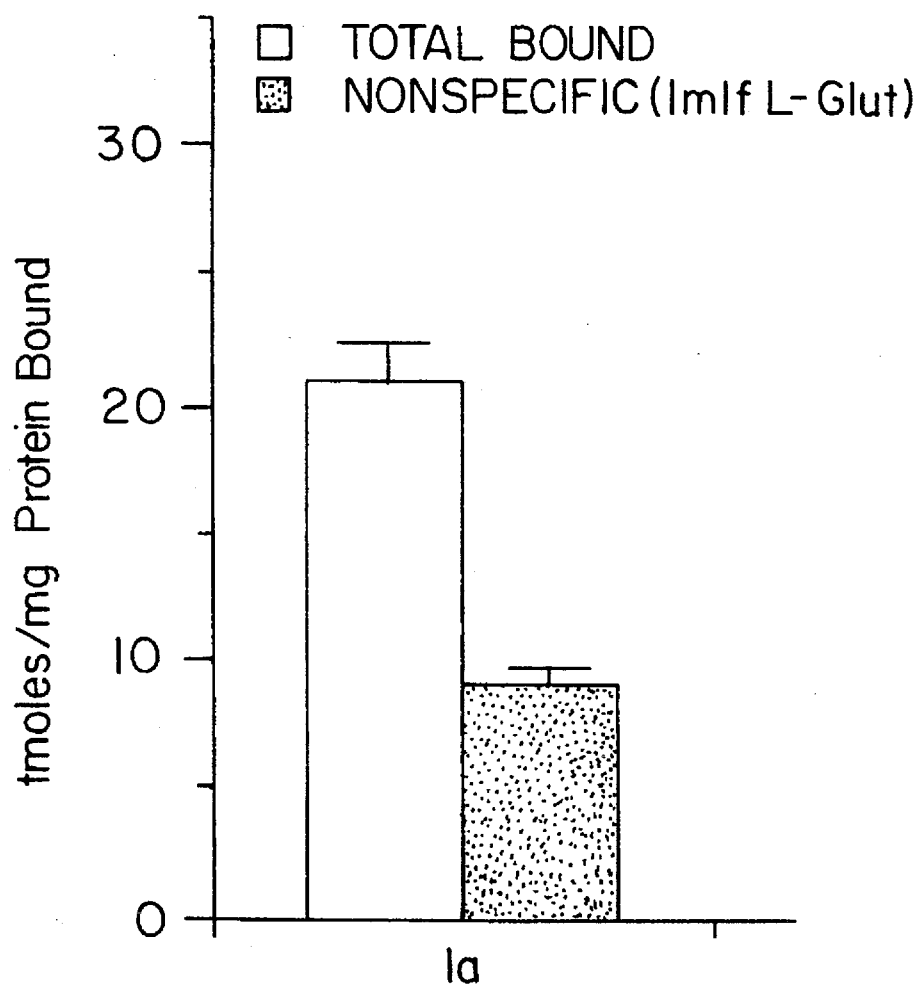

Assays performed in this manner, using membrane preparations derived from the EAA1a-producing COS cells, revealed specific [3H]-kainate binding at 5 nM and [3H]-glutamate binding at 10 nM, labelled ligand (FIG. 5). Mock transfected cells exhibited no specific binding of any of the ligands tested. These results demonstrate clearly that the human EAA1a receptor is binding kainate with high affinity. This activity, coupled with the fact that there is little or no demonstrable binding of either AMPA or NMDA clearly assigns the EAA1a receptor to be of the kainate type of EAA receptor. Furthermore, this binding profile, especially with the kainate binding being of the high affinity category (i.e. nonomolar range) indicates that the receptor is functioning in an authentic manner, and can therefore reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the EAA1a receptor gene in a pure form, capable of being expressed as a single, homogenous receptor species, therefore frees the ligand binding assay from the lack of precision introduced when complex, heterogeneous receptor preparations from human brains are used to attempt such characterizations.

EXAMPLE 5

Naturally occurring variants of the human EAA1a receptor

Figure 4A:
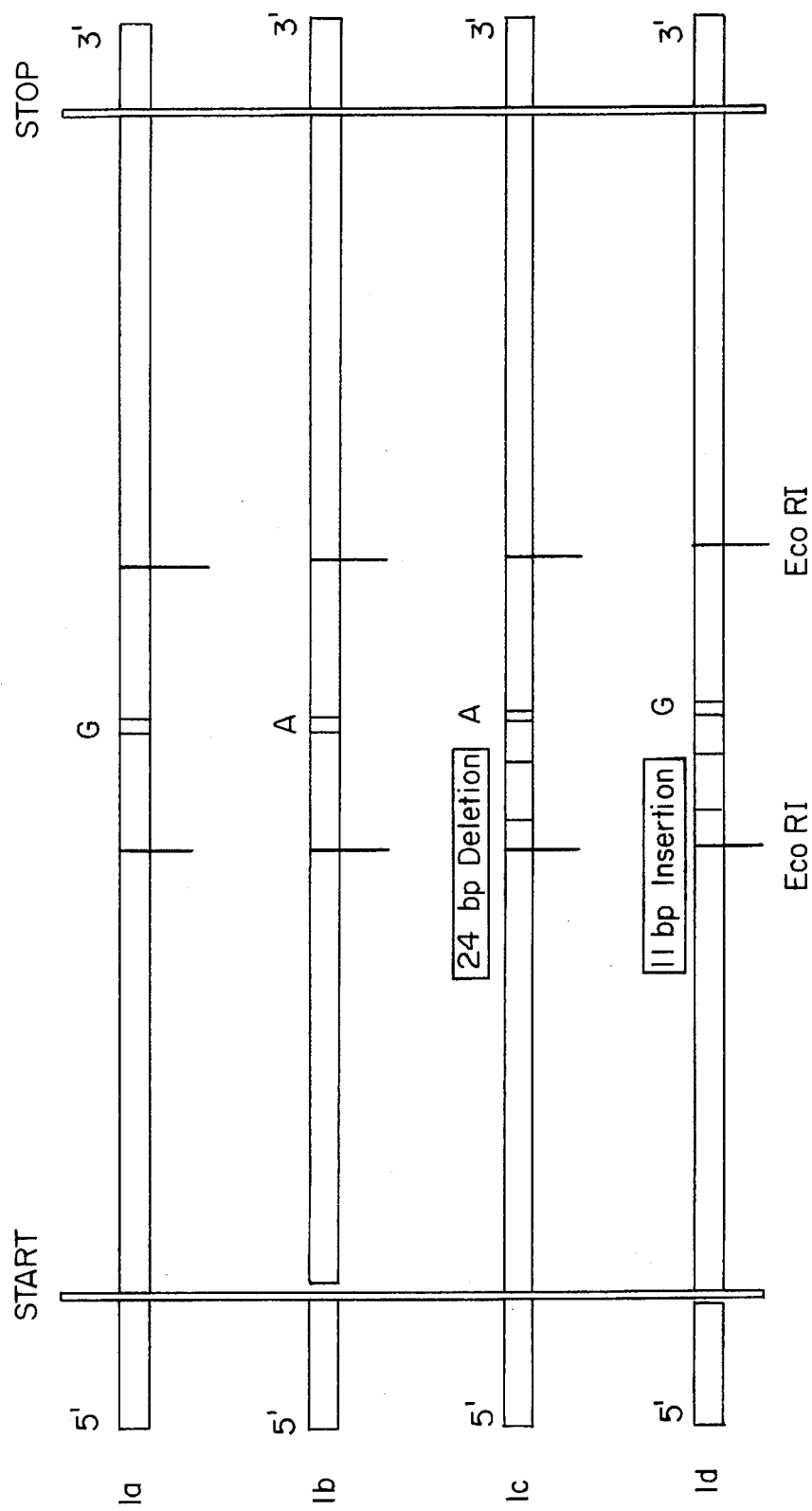

Using the same 1058bp probe which lead to the successful identification of the human EAA1a receptor, three sequence-related variants thereof were also identified and isolated, in substantially the same manner. As shown in FIGS. 4(a)–4(b) one variant designated EAA1d is similar in many structural respects to the human EAA1a receptor, and differs only by the precise insertion in EAA1d of an 11bp insertion, between nucleotide positions 1426 and 1427 of EAA1a. Like DNA coding for EAA1a, the EAA1d-encoding DNA was isolated from a cDNA library of human hippocampal DNA. To construct the full length cDNA containing the entire open reading frame, overlapping clones pBS/RKLS181 (representing the 5'-region) and pBS/RKLS911 (representing the 3'-region) were combined using the strategy shown in FIG. 3(b). For binding studies, the isolated cDNA insert has ben released from pBShumEAA1d-NotI, as a 3.7kb NotI/NotI fragment, and has been introduced for transient expression into cells of the COS-1 lineage after insertion into the vector pcDNA1 and, for stable expression, into CHO K1 or CHO Pro5 cells after insertion into vectors pcDNA1/NEO and pRC/CMV, all in the same manner as described above for human EAA1a.

A plasmid, designated pBS/humEAA1d-NotI, which carries a 3.7kb NotI/NotI cDNA insert coding for the human EAA1d receptor in a 3.0kb Bluescript-SK background, has been deposited, under the terms of the Budapest Treaty, with the American Type Culture Collection in Rockville, Md. USA on Aug. 21, 1991, under accession number ATCC 75064.

Another variant uncovered in the human hippocampal cDNA library using the same cloning strategy, designated the human EAA1b receptor, is nearly identical in all respects to EAA1a, except for a single nucleotide difference at position #1737 which results in a valine to isoleucine change within the extracellular N-terminal region of EAA1a, as shown in FIG. 4. DNA coding for a third variant designated human EAA1c was also isolated using the herein described cloning strategy and the human hippocampal cDNA library, carries a 24bp (8 amino acid) deletion relative to EAA1a, in the extracellular N-terminal region thereof (FIGS. 4(a) and (b).

We claim:

1. An isolated polynucleotide that codes for
    an EAA1a receptor having the amino acid sequence of 1–936 of SEQ ID NO: 2;
    an EAA1b receptor having the amino acid sequence of 1–936 of SEQ ID NO: 2 wherein the amino acid at position 508 is isoleucine;
    an EAA1c receptor wherein the polynucleotide coding for said receptor includes nucleotides 216 to 3023 of SEQ ID NO: 1 or degenerate codon equivalents thereof, in which nucleotides 1427–1450 are deleted and the codon at position 1713 encodes isoleucine; and
    an EAA1d receptor, wherein the polynucleotide coding for said receptor includes nucleotides 216–3023 of SEQ ID NO: 1, or degenerate codon equivalents thereof, in which nucleotides 1412–1460 are replaced by SEQ ID NO: 13.

2. An isolated polynucleotide according to claim 1, consisting of DNA.

3. An isolated polynucleotide according to claim 1, that codes for the human EAA1a receptor.

4. An isolated polynucleotide according to claim 1, that codes for the human EAA1b receptor.

5. An isolated polynucleotide according to claim 1, that codes for the human EAA1c receptor.

6. An isolated polynucleotide according to claim 1, that codes for the human EAA1d receptor.

7. A polynucleotide as defined in claim 1, which encodes said EAA1a receptor and has the nucleotide sequence of nucleotides 216–3023 of SEQ ID NO:1.

8. A polynucleotide as defined in claim 1, which encodes said EAA1b and has the nucleotide sequence of nucleotides 216–3023 of SEQ ID NO:1 with the exception that the nucleotide at position 1737 is adenosine.

9. A vector having incorporated therein a polynucleotide as defined in claim 1.

10. A vector according to claim 9, wherein said polynucleotide encodes the human EAA1a receptor.

11. A vector according to claim 10, wherein said vector is plasmid pBS/humanEAA1a-NotI (ATCC 75063).

12. A vector according to claim 9, wherein said polynucleotide encodes the human EAA1b receptor.

13. A vector according to claim 9, wherein said polynucleotide encodes the human EAA1c receptor.

14. A vector according to claim 9, wherein said polynucleotide encodes the human EAA1d receptor.

15. A vector according to claim 14, wherein said vector is plasmid pBS/humanEAA1d-NotI (ATCC 75064).

16. A cell that has been genetically engineered to produce a kainate-binding human EAA1 receptor, said cell having incorporated expressibly therein a polynucleotide as defined in claim 1.

17. A cell according to claim 16, wherein said heterologous polynucleotide codes for the human EAA1a receptor.

18. A membrane preparation derived from a cell as defined in claim 17.

19. A cell according to claim 16, wherein said heterologous polynucleotide codes for the human EAA1b receptor.

20. A cell according to claim 16, wherein said heterologous polynucleotide codes for the human EAA1c receptor.

21. A cell according to claim 16, wherein said heterologous polynucleotide codes for the human EAA1d receptor.

22. A membrane preparation derived from a cell as defined in claim 16.

23. A cell as defined in claim 16 which is a eukaryotic cell.

24. A cell according to claim 23, wherein said cell is a mammalian cell.

25. An oligonucleotide probe capable of hybridizing under stringent conditions with a polynucleotide that codes for a human EAA1a receptor having an amino acid sequence of residues 1–936 of SEQ ID NO:2, said probe being selected from the group of nucleotides consisting of nucleotides 1–3708, 8–156, 157–1563, 531–575, 1278–1359, 2826–2909, 2958–3073 and 3024–3708 of SEQ ID NO:1.

26. An oligonucleotide probe as claimed in claim 25, selected from the group of nucleotides consisting of nucleotides 1–3708, 8–156, 531–575, 1278–1359, 2826–2909, 2958–3073 and 3024–3708 of SEQ ID NO:1.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 3708 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 156..3026

( i x ) FEATURE:
        ( A ) NAME/KEY: sig_peptide
        ( B ) LOCATION: 156..215

( i x ) FEATURE:
        ( A ) NAME/KEY: mat_peptide
        ( B ) LOCATION: 216..3026

( x i ) SEQUENCE DESCRIPTION: SEQ ID NO:1:

```
GAATTCCCTG AGTGCCTACT ATGTGCCAGC CTGTGCTAGG CACTGAGGAC ACAGGTGGAA          60

AAGCCCGAAT TGCTCCCTGC TCTCCTGGCG CTCATCACCC CGGAGAGTTA TGTCATGCCC         120

AGGCCAGCAG GGGGCTCCAT GAGGATTCAT AGAAG ATG CCC CGC GTC TCG GCG            173
                                       Met Pro Arg Val Ser Ala
                                       -20                 -15

CCT TTG GTG CTG CTT CCT GCG TGG CTC GTG ATG GTC GCC TGC AGC CCG           221
Pro Leu Val Leu Leu Pro Ala Trp Leu Val Met Val Ala Cys Ser Pro
            -10              -5                               1

CAC TCC TTG AGG ATC GCT GCT ATC TTG GAC GAC CCC ATG GAG TGC AGC           269
His Ser Leu Arg Ile Ala Ala Ile Leu Asp Asp Pro Met Glu Cys Ser
          5              10                  15

AGA GGG GAG CGG CTC TCC ATC ACC CTG GCC AAG AAC CGC ATC AAC CGC           317
Arg Gly Glu Arg Leu Ser Ile Thr Leu Ala Lys Asn Arg Ile Asn Arg
     20              25                  30

GCT CCT GAG AGG CTG GGC AAG GCC AAG GTC GAA GTG GAC ATC TTT GAG           365
Ala Pro Glu Arg Leu Gly Lys Ala Lys Val Glu Val Asp Ile Phe Glu
35              40                  45                       50

CTT CTC AGA GAC AGC GAG TAC GAG ACT GCA GAA ACC ATG TGT CAG ATC           413
Leu Leu Arg Asp Ser Glu Tyr Glu Thr Ala Glu Thr Met Cys Gln Ile
              55                  60                  65

CTC CCC AAG GGG GTG GTC GCT GTC CTC GGA CCA TCG TCC AGC CCA GCC           461
Leu Pro Lys Gly Val Val Ala Val Leu Gly Pro Ser Ser Ser Pro Ala
         70                  75                  80

TCC AGC TCC ATC ATC AGC AAC ATC TGT GGA GAG AAG GAG GTC CCT CAC           509
Ser Ser Ser Ile Ile Ser Asn Ile Cys Gly Glu Lys Glu Val Pro His
             85                  90                  95

TTC AAA GTG GCC CCA GAG GAG TTC GTC AAG TTC CAG TTC CAG AGA TTC           557
Phe Lys Val Ala Pro Glu Glu Phe Val Lys Phe Gln Phe Gln Arg Phe
100                 105                 110

ACA ACC CTG AAC CTC CAC CCC AGC AAC ACT GAC ATC AGC GTG GCT GTA           605
Thr Thr Leu Asn Leu His Pro Ser Asn Thr Asp Ile Ser Val Ala Val
115                 120                 125                 130

GCT GGG ATC CTG AAC TTC TTC AAC TGC ACC ACC GCC TGC CTC ATC TGT           653
Ala Gly Ile Leu Asn Phe Phe Asn Cys Thr Thr Ala Cys Leu Ile Cys
             135                 140                 145

GCC AAA GCA GAA TGC CTT TTA AAC CTA GAG AAG CTG CTC CGG CAA TTC           701
Ala Lys Ala Glu Cys Leu Leu Asn Leu Glu Lys Leu Leu Arg Gln Phe
         150                 155                 160

CTT ATC TCC AAG GAC ACG CTG TCC GTC CGC ATG CTG GAT GAC ACC CGG           749
```

-continued

| | | | | | | | | | | | | | | |
|---|---|---|---|---|---|---|---|---|---|---|---|---|---|---|
| Leu | Ile | Ser | Lys | Asp | Thr | Leu | Ser | Val | Arg | Met | Leu | Asp | Asp | Thr | Arg |
| | | 165 | | | | | 170 | | | | | 175 | | |

| GAC | CCC | ACC | CCG | CTC | CTC | AAG | GAG | ATC | CGG | GAC | GAC | AAG | ACC | GCC | ACC | 797 |
|---|---|---|---|---|---|---|---|---|---|---|---|---|---|---|---|---|
| Asp | Pro | Thr | Pro | Leu | Leu | Lys | Glu | Ile | Arg | Asp | Asp | Lys | Thr | Ala | Thr | |
| 180 | | | | | 185 | | | | | | 190 | | | | | |

| ATC | ATC | ATC | CAC | GCC | AAC | GCC | TCC | ATG | TCC | CAC | ACC | ATC | CTC | CTG | AAG | 845 |
|---|---|---|---|---|---|---|---|---|---|---|---|---|---|---|---|---|
| Ile | Ile | Ile | His | Ala | Asn | Ala | Ser | Met | Ser | His | Thr | Ile | Leu | Leu | Lys | |
| 195 | | | | | 200 | | | | | 205 | | | | | 210 | |

| GCA | GCC | GAA | CTT | GGG | ATG | GTG | TCA | GCC | TAT | TAC | ACA | TAC | ATC | TTC | ACT | 893 |
|---|---|---|---|---|---|---|---|---|---|---|---|---|---|---|---|---|
| Ala | Ala | Glu | Leu | Gly | Met | Val | Ser | Ala | Tyr | Tyr | Thr | Tyr | Ile | Phe | Thr | |
| | | | | 215 | | | | 220 | | | | | 225 | | | |

| AAT | CTG | GAG | TTC | TCA | CTC | CAG | AGA | ACG | GAC | AGC | CTT | GTG | GAT | GAT | CGT | 941 |
|---|---|---|---|---|---|---|---|---|---|---|---|---|---|---|---|---|
| Asn | Leu | Glu | Phe | Ser | Leu | Gln | Arg | Thr | Asp | Ser | Leu | Val | Asp | Asp | Arg | |
| | | 230 | | | | | 235 | | | | | 240 | | | | |

| GTC | AAC | ATC | CTG | GGA | TTT | TCC | ATT | TTC | AAC | CAA | TCC | CAT | GCT | TTC | TTC | 989 |
|---|---|---|---|---|---|---|---|---|---|---|---|---|---|---|---|---|
| Val | Asn | Ile | Leu | Gly | Phe | Ser | Ile | Phe | Asn | Gln | Ser | His | Ala | Phe | Phe | |
| | | 245 | | | | 250 | | | | | 255 | | | | | |

| CAA | GAG | TTT | GCC | CAG | AGC | CTC | AAC | CAG | TCC | TGG | CAG | GAG | AAC | TGT | GAC | 1037 |
|---|---|---|---|---|---|---|---|---|---|---|---|---|---|---|---|---|
| Gln | Glu | Phe | Ala | Gln | Ser | Leu | Asn | Gln | Ser | Trp | Gln | Glu | Asn | Cys | Asp | |
| 260 | | | | | 265 | | | | | 270 | | | | | | |

| CAT | GTG | CCC | TTC | ACT | GGG | CCT | GCG | CTC | TCC | TCG | GCC | CTG | CTG | TTT | GAT | 1085 |
|---|---|---|---|---|---|---|---|---|---|---|---|---|---|---|---|---|
| His | Val | Pro | Phe | Thr | Gly | Pro | Ala | Leu | Ser | Ser | Ala | Leu | Leu | Phe | Asp | |
| 275 | | | | 280 | | | | | 285 | | | | | 290 | | |

| GCT | GTC | TAT | GCT | GTG | GTG | ACT | GCG | GTG | CAG | GAA | CTG | AAC | CGG | AGC | CAA | 1133 |
|---|---|---|---|---|---|---|---|---|---|---|---|---|---|---|---|---|
| Ala | Val | Tyr | Ala | Val | Val | Thr | Ala | Val | Gln | Glu | Leu | Asn | Arg | Ser | Gln | |
| | | | | 295 | | | | | 300 | | | | | 305 | | |

| GAG | ATC | GGC | GTG | AAG | CCC | TTG | TCC | TGC | GGC | TCG | GCC | CAG | ATC | TGG | CAG | 1181 |
|---|---|---|---|---|---|---|---|---|---|---|---|---|---|---|---|---|
| Glu | Ile | Gly | Val | Lys | Pro | Leu | Ser | Cys | Gly | Ser | Ala | Gln | Ile | Trp | Gln | |
| | | | 310 | | | | | 315 | | | | | 320 | | | |

| CAC | GGC | ACC | AGC | CTC | ATG | AAC | TAC | CTG | CGC | ATG | GTA | GAA | TTG | GAA | GGT | 1229 |
|---|---|---|---|---|---|---|---|---|---|---|---|---|---|---|---|---|
| His | Gly | Thr | Ser | Leu | Met | Asn | Tyr | Leu | Arg | Met | Val | Glu | Leu | Glu | Gly | |
| | | 325 | | | | | 330 | | | | | 335 | | | | |

| CTT | ACC | GGC | CAC | ATT | GAA | TTC | AAC | AGC | AAA | GGC | CAG | AGG | TCC | AAC | TAC | 1277 |
|---|---|---|---|---|---|---|---|---|---|---|---|---|---|---|---|---|
| Leu | Thr | Gly | His | Ile | Glu | Phe | Asn | Ser | Lys | Gly | Gln | Arg | Ser | Asn | Tyr | |
| | 340 | | | | | 345 | | | | | 350 | | | | | |

| GCT | TTG | AAA | ATC | TTA | CAG | TTC | ACA | AGG | AAT | GGT | TTT | CGG | CAG | ATC | GGC | 1325 |
|---|---|---|---|---|---|---|---|---|---|---|---|---|---|---|---|---|
| Ala | Leu | Lys | Ile | Leu | Gln | Phe | Thr | Arg | Asn | Gly | Phe | Arg | Gln | Ile | Gly | |
| 355 | | | | | 360 | | | | | 365 | | | | | 370 | |

| CAG | TGG | CAC | GTG | GCA | GAG | GGC | CTC | AGC | ATG | GAC | AGC | CAC | CTC | TAT | GCC | 1373 |
|---|---|---|---|---|---|---|---|---|---|---|---|---|---|---|---|---|
| Gln | Trp | His | Val | Ala | Glu | Gly | Leu | Ser | Met | Asp | Ser | His | Leu | Tyr | Ala | |
| | | | | 375 | | | | | 380 | | | | | 385 | | |

| TCC | AAC | ATC | TCG | GAC | ACT | CTC | TTC | AAC | ACC | ACC | CTG | GTC | GTC | ACC | ACC | 1421 |
|---|---|---|---|---|---|---|---|---|---|---|---|---|---|---|---|---|
| Ser | Asn | Ile | Ser | Asp | Thr | Leu | Phe | Asn | Thr | Thr | Leu | Val | Val | Thr | Thr | |
| | | | 390 | | | | | 395 | | | | | 400 | | | |

| ATC | CTG | GAA | AAC | CCA | TAT | TTA | ATG | CTG | AAG | GGG | AAC | CAC | CAG | GAG | ATG | 1469 |
|---|---|---|---|---|---|---|---|---|---|---|---|---|---|---|---|---|
| Ile | Leu | Glu | Asn | Pro | Tyr | Leu | Met | Leu | Lys | Gly | Asn | His | Gln | Glu | Met | |
| | | 405 | | | | | 410 | | | | | 415 | | | | |

| GAA | GGC | AAT | GAC | CGC | TAC | GAG | GGC | TTC | TGT | GTG | GAC | ATG | CTC | AAG | GAG | 1517 |
|---|---|---|---|---|---|---|---|---|---|---|---|---|---|---|---|---|
| Glu | Gly | Asn | Asp | Arg | Tyr | Glu | Gly | Phe | Cys | Val | Asp | Met | Leu | Lys | Glu | |
| | 420 | | | | | 425 | | | | | 430 | | | | | |

| CTG | GCA | GAG | ATC | CTC | CGA | TTC | AAC | TAC | AAG | ATC | CGC | CTG | GTT | GGG | GAT | 1565 |
|---|---|---|---|---|---|---|---|---|---|---|---|---|---|---|---|---|
| Leu | Ala | Glu | Ile | Leu | Arg | Phe | Asn | Tyr | Lys | Ile | Arg | Leu | Val | Gly | Asp | |
| 435 | | | | | 440 | | | | | 445 | | | | | 450 | |

| GGC | GTG | TAC | GGC | GTT | CCC | GAG | GCC | AAC | GGC | ACC | TGG | ACG | GGA | ATG | GTC | 1613 |
|---|---|---|---|---|---|---|---|---|---|---|---|---|---|---|---|---|
| Gly | Val | Tyr | Gly | Val | Pro | Glu | Ala | Asn | Gly | Thr | Trp | Thr | Gly | Met | Val | |
| | | | | 455 | | | | | 460 | | | | | 465 | | |

| GGG | GAG | CTG | ATC | GCT | AGG | AAA | GCA | GAT | CTG | GCT | GTG | GCA | GGC | CTC | ACC | 1661 |
|---|---|---|---|---|---|---|---|---|---|---|---|---|---|---|---|---|
| Gly | Glu | Leu | Ile | Ala | Arg | Lys | Ala | Asp | Leu | Ala | Val | Ala | Gly | Leu | Thr | |
| | | | 470 | | | | | 475 | | | | | 480 | | | |

| ATT | ACA | GCT | GAA | CGG | GAG | AAG | GTG | ATT | GAT | TTC | TCT | AAG | CCA | TTC | ATG | 1709 |
|---|---|---|---|---|---|---|---|---|---|---|---|---|---|---|---|---|

```
Ile Thr Ala Glu Arg Glu Lys Val Ile Asp Phe Ser Lys Pro Phe Met
    485                 490                 495

ACT CTG GGA ATT AGC ATT CTT TAC CGC GTT CAT ATG GGA CGC AAA CCC      1757
Thr Leu Gly Ile Ser Ile Leu Tyr Arg Val His Met Gly Arg Lys Pro
    500                 505                 510

GGC TAT TTC TCC TTC CTG GAC CCA TTT TCT CCG GGC GTC TGG CTC TTC      1805
Gly Tyr Phe Ser Phe Leu Asp Pro Phe Ser Pro Gly Val Trp Leu Phe
515                     520                 525                 530

ATG CTT CTA GCC TAT CTG GCC GTC AGC TGT GTC CTC TTC CTG GTG GCT      1853
Met Leu Leu Ala Tyr Leu Ala Val Ser Cys Val Leu Phe Leu Val Ala
                535                 540                 545

CGG TTG ACG CCC TAC GAG TGG TAC AGC CCA CAC CCA TGT GCC CAG GGC      1901
Arg Leu Thr Pro Tyr Glu Trp Tyr Ser Pro His Pro Cys Ala Gln Gly
            550                 555                 560

CGG TGC AAC CTC CTG GTG AAC CAG TAC TCC CTG GGC AAC AGC CTC TGG      1949
Arg Cys Asn Leu Leu Val Asn Gln Tyr Ser Leu Gly Asn Ser Leu Trp
        565                 570                 575

TTT CCG GTC GGG GGG TTC ATG CAG CAG GGC TCC ACC ATC GCC CCT CGC      1997
Phe Pro Val Gly Gly Phe Met Gln Gln Gly Ser Thr Ile Ala Pro Arg
    580                 585                 590

GCC TTA TCC ACC CGC TGT GTC AGT GGC GTC TGG TGG GCA TTC ACG CTG      2045
Ala Leu Ser Thr Arg Cys Val Ser Gly Val Trp Trp Ala Phe Thr Leu
595                 600                 605                     610

ATC ATC ATC TCA TCC TAC ACG GCC AAC CTG GCA GCC TTC CTG ACC GTG      2093
Ile Ile Ile Ser Ser Tyr Thr Ala Asn Leu Ala Ala Phe Leu Thr Val
                615                 620                 625

CAG CGC ATG GAT GTG CCC ATT GAG TCA GTG GAT GAC CTG GCT GAC CAG      2141
Gln Arg Met Asp Val Pro Ile Glu Ser Val Asp Asp Leu Ala Asp Gln
            630                 635                 640

ACC GCC ATT GAA TAT GGC ACA ATT CAC GGA GGC TCC AGC ATG ACC TTC      2189
Thr Ala Ile Glu Tyr Gly Thr Ile His Gly Gly Ser Ser Met Thr Phe
        645                 650                 655

TTC CAA AAT TCC CGC TAC CAG ACC TAC CAA CGC ATG TGG AAT TAC ATG      2237
Phe Gln Asn Ser Arg Tyr Gln Thr Tyr Gln Arg Met Trp Asn Tyr Met
    660                 665                 670

TAT TCC AAG CAG CCC AGC GTG TTC GTG AAG AGC ACA GAG GAG GGA ATC      2285
Tyr Ser Lys Gln Pro Ser Val Phe Val Lys Ser Thr Glu Glu Gly Ile
675                 680                 685                     690

GCC AGG GTG TTG AAT TCC AAC TAC GCC TTC CTC CTG GAA TCC ACC ATG      2333
Ala Arg Val Leu Asn Ser Asn Tyr Ala Phe Leu Leu Glu Ser Thr Met
                695                 700                 705

AAC GAG TAC TAT CGG CAG CGA AAC TGC AAC CTC ACT CAG ATT GGG GGC      2381
Asn Glu Tyr Tyr Arg Gln Arg Asn Cys Asn Leu Thr Gln Ile Gly Gly
            710                 715                 720

CTG CTG GAC ACC AAG GGC TAT GGG ATT GGC ATG CCA GTC GGC TCG GTT      2429
Leu Leu Asp Thr Lys Gly Tyr Gly Ile Gly Met Pro Val Gly Ser Val
        725                 730                 735

TTC CGG GAC GAG TTT GAT CTG GCC ATT CTC CAG CTG CAG GAG AAC AAC      2477
Phe Arg Asp Glu Phe Asp Leu Ala Ile Leu Gln Leu Gln Glu Asn Asn
    740                 745                 750

CGC CTG GAG ATC CTG AAG CGC AAA TGG TGG GAA GGA GGG AAG TGC CCC      2525
Arg Leu Glu Ile Leu Lys Arg Lys Trp Trp Glu Gly Gly Lys Cys Pro
755                 760                 765                     770

AAG GAG GAA GAT CAC AGA GCT AAA GGC CTG GGA ATG GAG AAT ATT GGT      2573
Lys Glu Glu Asp His Arg Ala Lys Gly Leu Gly Met Glu Asn Ile Gly
                775                 780                 785

GGA ATC TTT GTG GTT CTT ATT TGT GGC TTA ATC GTG GCC ATT TTT ATG      2621
Gly Ile Phe Val Val Leu Ile Cys Gly Leu Ile Val Ala Ile Phe Met
            790                 795                 800

GCT ATG TTG GAG TTT TTA TGG ACT CTC AGA CAC TCA GAA GCA ACT GAG      2669
```

```
Ala  Met  Leu  Glu  Phe  Leu  Trp  Thr  Leu  Arg  His  Ser  Glu  Ala  Thr  Glu
     805                 810                     815

GTG  TCC  GTC  TGC  CAG  GAG  ATG  GTG  ACC  GAG  CTG  CGC  AGC  ATT  ATC  CTG   2717
Val  Ser  Val  Cys  Gln  Glu  Met  Val  Thr  Glu  Leu  Arg  Ser  Ile  Ile  Leu
     820                 825                     830

TGT  CAG  GAC  AGT  ATC  CAC  CCC  CGC  CGG  CGG  CGC  GCC  GCA  GTC  CCG  CCG   2765
Cys  Gln  Asp  Ser  Ile  His  Pro  Arg  Arg  Arg  Arg  Ala  Ala  Val  Pro  Pro
835                      840                     845                      850

CCC  CGG  CCC  CCC  ATC  CCC  GAG  GAG  CGC  CGA  CCG  CGG  GGC  ACG  GCG  ACG   2813
Pro  Arg  Pro  Pro  Ile  Pro  Glu  Glu  Arg  Arg  Pro  Arg  Gly  Thr  Ala  Thr
               855                      860                           865

CTC  AGC  AAC  GGG  AAG  CTG  TGC  GGG  GCA  GGG  GAG  CCC  GAC  CAG  CTC  GCG   2861
Leu  Ser  Asn  Gly  Lys  Leu  Cys  Gly  Ala  Gly  Glu  Pro  Asp  Gln  Leu  Ala
               870                 875                           880

CAG  AGA  CTG  GCG  CAG  GAG  GCC  GCC  CTG  GTG  GCC  CGC  GGC  TGC  ACG  CAC   2909
Gln  Arg  Leu  Ala  Gln  Glu  Ala  Ala  Leu  Val  Ala  Arg  Gly  Cys  Thr  His
          885                      890                      895

ATC  CGC  GTC  TGC  CCC  GAG  TGC  CGC  CGC  TTC  CAG  GGC  CTG  CGG  GCA  CGG   2957
Ile  Arg  Val  Cys  Pro  Glu  Cys  Arg  Arg  Phe  Gln  Gly  Leu  Arg  Ala  Arg
     900                      905                      910

CCG  TCG  CCC  GCC  CGC  AGC  GAG  GAG  AGC  CTG  GAG  TGG  GAG  AAA  ACC  ACC   3005
Pro  Ser  Pro  Ala  Arg  Ser  Glu  Glu  Ser  Leu  Glu  Trp  Glu  Lys  Thr  Thr
915                      920                      925                      930

AAC  AGC  AGC  GAG  CCC  GAG  TAGTCCCGGA  GGCCACAGGA  CGCGCAGAGG                 3053
Asn  Ser  Ser  Glu  Pro  Glu
                    935

CCGGGCGGGG  CGGGAGGGGA  GGGGCGGGGC  GGGCGCTGCT  GTCAGCCGCC  AGCCGGAACT          3113
TGTACAGCGT  CGACACCTCT  CCAGATTTCG  GATCCAGTCA  CTTTTCAAAA  AGATCAAGGA          3173
GCCTGACGCC  CCAGCCAGAG  ACCGCGCCCG  GTCAGGGAGC  AGGGTCCACC  CGGAAACGTT          3233
GCACCCAAAG  GGCAAGGAC   GGCCCTCCCT  CCTGGGCACA  AGGACCCATC  TTCTCCCAGT          3293
GGGTCTTTCC  CTCTCGCCAA  AATAACAAGA  GTATAGGGTG  GGGGGTCCCT  ACCCAGACCA          3353
GTCCAATGAA  TTGGTGGAAT  CATCAGTTGA  ATTTCCCCCT  AGTCAGGGGC  AATGTACCC           3413
TCCGTCTAGT  TCTTACAGAA  AAAAAAAAA   ATTAAACAGG  GAAGTTTTC   TTTTCTGGAT          3473
TTGTATATTT  TTGTTAATGT  TCTTTTCCCT  TTTCTTTCCT  CCTCTCCTTT  TCTTCTTTGT          3533
CATCTTCTCA  GTCCTGTTAA  TTTGTTTTGT  GTTTTTTGGA  GGGGGAGGCT  GGGTTAGGGA          3593
ATGGAAGCCT  AAATAATCCC  TATTTCTTCT  TTTTCCTGAA  TTTTGGAATA  TTGCGTTACC          3653
AGTGCATCCG  ATTTCAGGTG  CGGAACTCTC  TGTATGGTGA  CTGAGGGGCC  TGCAG              3708
```

( 2 ) INFORMATION FOR SEQ ID NO:2:

( i ) SEQUENCE CHARACTERISTICS:
        ( A ) LENGTH: 956 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Pro  Arg  Val  Ser  Ala  Pro  Leu  Val  Leu  Pro  Ala  Trp  Leu  Val
-20                 -15                 -10                           -5

Met  Val  Ala  Cys  Ser  Pro  His  Ser  Leu  Arg  Ile  Ala  Ala  Ile  Leu  Asp
                    1                   5                        10

Asp  Pro  Met  Glu  Cys  Ser  Arg  Gly  Glu  Arg  Leu  Ser  Ile  Thr  Leu  Ala
          15                  20                      25

Lys  Asn  Arg  Ile  Asn  Arg  Ala  Pro  Glu  Arg  Leu  Gly  Lys  Ala  Lys  Val
     30                  35                      40
```

-continued

| | | | | | | | | | | | | | | |
|---|---|---|---|---|---|---|---|---|---|---|---|---|---|---|
| Glu | Val | Asp | Ile | Phe | Glu | Leu | Leu | Arg | Asp | Ser | Glu | Tyr | Glu | Thr | Ala |
| 45 | | | | 50 | | | | 55 | | | | | | 60 |
| Glu | Thr | Met | Cys | Gln | Ile | Leu | Pro | Lys | Gly | Val | Val | Ala | Val | Leu | Gly |
| | | | 65 | | | | 70 | | | | | 75 | | |
| Pro | Ser | Ser | Ser | Pro | Ala | Ser | Ser | Ser | Ile | Ile | Ser | Asn | Ile | Cys | Gly |
| | | | 80 | | | | | 85 | | | | | 90 | | |
| Glu | Lys | Glu | Val | Pro | His | Phe | Lys | Val | Ala | Pro | Glu | Glu | Phe | Val | Lys |
| | | 95 | | | | | 100 | | | | | 105 | | | |
| Phe | Gln | Phe | Gln | Arg | Phe | Thr | Thr | Leu | Asn | Leu | His | Pro | Ser | Asn | Thr |
| | 110 | | | | | 115 | | | | | 120 | | | | |
| Asp | Ile | Ser | Val | Ala | Val | Ala | Gly | Ile | Leu | Asn | Phe | Phe | Asn | Cys | Thr |
| 125 | | | | | 130 | | | | | 135 | | | | | 140 |
| Thr | Ala | Cys | Leu | Ile | Cys | Ala | Lys | Ala | Glu | Cys | Leu | Leu | Asn | Leu | Glu |
| | | | | 145 | | | | | 150 | | | | | 155 | |
| Lys | Leu | Leu | Arg | Gln | Phe | Leu | Ile | Ser | Lys | Asp | Thr | Leu | Ser | Val | Arg |
| | | | 160 | | | | | 165 | | | | | 170 | | |
| Met | Leu | Asp | Asp | Thr | Arg | Asp | Pro | Thr | Pro | Leu | Leu | Lys | Glu | Ile | Arg |
| | | 175 | | | | | 180 | | | | | 185 | | | |
| Asp | Asp | Lys | Thr | Ala | Thr | Ile | Ile | Ile | His | Ala | Asn | Ala | Ser | Met | Ser |
| | 190 | | | | | 195 | | | | | 200 | | | | |
| His | Thr | Ile | Leu | Leu | Lys | Ala | Ala | Glu | Leu | Gly | Met | Val | Ser | Ala | Tyr |
| 205 | | | | | 210 | | | | | 215 | | | | | 220 |
| Tyr | Thr | Tyr | Ile | Phe | Thr | Asn | Leu | Glu | Phe | Ser | Leu | Gln | Arg | Thr | Asp |
| | | | | 225 | | | | | 230 | | | | | 235 | |
| Ser | Leu | Val | Asp | Asp | Arg | Val | Asn | Ile | Leu | Gly | Phe | Ser | Ile | Phe | Asn |
| | | | 240 | | | | | 245 | | | | | 250 | | |
| Gln | Ser | His | Ala | Phe | Phe | Gln | Glu | Phe | Ala | Gln | Ser | Leu | Asn | Gln | Ser |
| | | 255 | | | | | 260 | | | | | 265 | | | |
| Trp | Gln | Glu | Asn | Cys | Asp | His | Val | Pro | Phe | Thr | Gly | Pro | Ala | Leu | Ser |
| | 270 | | | | | 275 | | | | | 280 | | | | |
| Ser | Ala | Leu | Leu | Phe | Asp | Ala | Val | Tyr | Ala | Val | Thr | Ala | Val | Gln |
| 285 | | | | | 290 | | | | | 295 | | | | | 300 |
| Glu | Leu | Asn | Arg | Ser | Gln | Glu | Ile | Gly | Val | Lys | Pro | Leu | Ser | Cys | Gly |
| | | | | 305 | | | | | 310 | | | | | 315 | |
| Ser | Ala | Gln | Ile | Trp | Gln | His | Gly | Thr | Ser | Leu | Met | Asn | Tyr | Leu | Arg |
| | | | 320 | | | | | 325 | | | | | 330 | | |
| Met | Val | Glu | Leu | Glu | Gly | Leu | Thr | Gly | His | Ile | Glu | Phe | Asn | Ser | Lys |
| | | 335 | | | | | 340 | | | | | 345 | | | |
| Gly | Gln | Arg | Ser | Asn | Tyr | Ala | Leu | Lys | Ile | Leu | Gln | Phe | Thr | Arg | Asn |
| | 350 | | | | | 355 | | | | | 360 | | | | |
| Gly | Phe | Arg | Gln | Ile | Gly | Gln | Trp | His | Val | Ala | Glu | Gly | Leu | Ser | Met |
| 365 | | | | | 370 | | | | | 375 | | | | | 380 |
| Asp | Ser | His | Leu | Tyr | Ala | Ser | Asn | Ile | Ser | Asp | Thr | Leu | Phe | Asn | Thr |
| | | | | 385 | | | | | 390 | | | | | 395 | |
| Thr | Leu | Val | Val | Thr | Thr | Ile | Leu | Glu | Asn | Pro | Tyr | Leu | Met | Leu | Lys |
| | | | 400 | | | | | 405 | | | | | 410 | | |
| Gly | Asn | His | Gln | Glu | Met | Glu | Gly | Asn | Asp | Arg | Tyr | Glu | Gly | Phe | Cys |
| | | 415 | | | | | 420 | | | | | 425 | | | |
| Val | Asp | Met | Leu | Lys | Glu | Leu | Ala | Glu | Ile | Leu | Arg | Phe | Asn | Tyr | Lys |
| | 430 | | | | | 435 | | | | | 440 | | | | |
| Ile | Arg | Leu | Val | Gly | Asp | Gly | Val | Tyr | Gly | Val | Pro | Glu | Ala | Asn | Gly |
| 445 | | | | | 450 | | | | | 455 | | | | | 460 |
| Thr | Trp | Thr | Gly | Met | Val | Gly | Glu | Leu | Ile | Ala | Arg | Lys | Ala | Asp | Leu |

|     |     |     |     |     |     | 465 |     |     |     |     | 470 |     |     |     |     | 475 |     |
|---|---|---|---|---|---|---|---|---|---|---|---|---|---|---|---|---|---|

```
Ala   Val   Ala   Gly   Leu   Thr   Ile   Thr   Ala   Glu   Arg   Glu   Lys   Val   Ile   Asp
                  480                     485                     490

Phe   Ser   Lys   Pro   Phe   Met   Thr   Leu   Gly   Ile   Ser   Ile   Leu   Tyr   Arg   Val
            495                     500                     505

His   Met   Gly   Arg   Lys   Pro   Gly   Tyr   Phe   Ser   Phe   Leu   Asp   Pro   Phe   Ser
      510                     515                     520

Pro   Gly   Val   Trp   Leu   Phe   Met   Leu   Leu   Ala   Tyr   Leu   Ala   Val   Ser   Cys
525                           530                     535                           540

Val   Leu   Phe   Leu   Val   Ala   Arg   Leu   Thr   Pro   Tyr   Glu   Trp   Tyr   Ser   Pro
                        545                     550                           555

His   Pro   Cys   Ala   Gln   Gly   Arg   Cys   Asn   Leu   Leu   Val   Asn   Gln   Tyr   Ser
                  560                     565                     570

Leu   Gly   Asn   Ser   Leu   Trp   Phe   Pro   Val   Gly   Gly   Phe   Met   Gln   Gln   Gly
            575                     580                     585

Ser   Thr   Ile   Ala   Pro   Arg   Ala   Leu   Ser   Thr   Arg   Cys   Val   Ser   Gly   Val
      590                     595                     600

Trp   Trp   Ala   Phe   Thr   Leu   Ile   Ile   Ile   Ser   Ser   Tyr   Thr   Ala   Asn   Leu
605                           610                     615                           620

Ala   Ala   Phe   Leu   Thr   Val   Gln   Arg   Met   Asp   Val   Pro   Ile   Glu   Ser   Val
                        625                     630                           635

Asp   Asp   Leu   Ala   Asp   Gln   Thr   Ala   Ile   Glu   Tyr   Gly   Thr   Ile   His   Gly
                  640                     645                     650

Gly   Ser   Ser   Met   Thr   Phe   Phe   Gln   Asn   Ser   Arg   Tyr   Gln   Thr   Tyr   Gln
            655                     660                     665

Arg   Met   Trp   Asn   Tyr   Met   Tyr   Ser   Lys   Gln   Pro   Ser   Val   Phe   Val   Lys
      670                     675                     680

Ser   Thr   Glu   Glu   Gly   Ile   Ala   Arg   Val   Leu   Asn   Ser   Asn   Tyr   Ala   Phe
685                           690                     695                           700

Leu   Leu   Glu   Ser   Thr   Met   Asn   Glu   Tyr   Tyr   Arg   Gln   Arg   Asn   Cys   Asn
                        705                     710                           715

Leu   Thr   Gln   Ile   Gly   Gly   Leu   Leu   Asp   Thr   Lys   Gly   Tyr   Gly   Ile   Gly
                  720                     725                     730

Met   Pro   Val   Gly   Ser   Val   Phe   Arg   Asp   Glu   Phe   Asp   Leu   Ala   Ile   Leu
            735                     740                     745

Gln   Leu   Gln   Glu   Asn   Asn   Arg   Leu   Glu   Ile   Leu   Lys   Arg   Lys   Trp   Trp
      750                     755                     760

Glu   Gly   Gly   Lys   Cys   Pro   Lys   Glu   Glu   Asp   His   Arg   Ala   Lys   Gly   Leu
765                           770                     775                           780

Gly   Met   Glu   Asn   Ile   Gly   Gly   Ile   Phe   Val   Val   Leu   Ile   Cys   Gly   Leu
                        785                     790                           795

Ile   Val   Ala   Ile   Phe   Met   Ala   Met   Leu   Glu   Phe   Leu   Trp   Thr   Leu   Arg
                  800                     805                     810

His   Ser   Glu   Ala   Thr   Glu   Val   Ser   Val   Cys   Gln   Glu   Met   Val   Thr   Glu
            815                     820                     825

Leu   Arg   Ser   Ile   Ile   Leu   Cys   Gln   Asp   Ser   Ile   His   Pro   Arg   Arg   Arg
      830                     835                     840

Arg   Ala   Ala   Val   Pro   Pro   Pro   Arg   Pro   Pro   Ile   Pro   Glu   Glu   Arg   Arg
845                           850                     855                           860

Pro   Arg   Gly   Thr   Ala   Thr   Leu   Ser   Asn   Gly   Lys   Leu   Cys   Gly   Ala   Gly
                        865                     870                           875

Glu   Pro   Asp   Gln   Leu   Ala   Gln   Arg   Leu   Ala   Gln   Glu   Ala   Ala   Leu   Val
                  880                     885                     890
```

```
Ala  Arg  Gly  Cys  Thr  His  Ile  Arg  Val  Cys  Pro  Glu  Cys  Arg  Arg  Phe
          895                      900                     905

Gln  Gly  Leu  Arg  Ala  Arg  Pro  Ser  Pro  Ala  Arg  Ser  Glu  Glu  Ser  Leu
          910                      915                     920

Glu  Trp  Glu  Lys  Thr  Thr  Asn  Ser  Ser  Glu  Pro  Glu
925                      930                     935
```

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:3:

GGGGTTTAAG CTTCTGAGTG CCTACTATGT GCCCAG                                  36

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:4:

GGGTGGGGTC CCGGGTGTCA TC                                                  22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:5:

GATGACACCC GGGACCCCAC CC                                                  22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:6:

TGCGTCCCAT ATGAATGCGG TA                                                  22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single (D) TOPOLOGY: linear (i i) MOLECULE TYPE: Other nucleic acid;
  (A) DESCRIPTION: Synthetic DNA oligonucleotide (x i) SEQUENCE DESCRIPTION: SEQ ID NO:7:

TACCGCATTC ATATGGGACG CA  22

(2) INFORMATION FOR SEQ ID NO:8:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (i i) MOLECULE TYPE: Other nucleic acid;
    (A) DESCRIPTION: Synthetic DNA oligonucleotide (x i) SEQUENCE DESCRIPTION: SEQ ID NO:8:

GAGGTGTCGA CGCTGTACAA GT  22

(2) INFORMATION FOR SEQ ID NO:9:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (i i) MOLECULE TYPE: Other nucleic acid;
    (A) DESCRIPTION: Synthetic DNA oligonucleotide (x i) SEQUENCE DESCRIPTION: SEQ ID NO:9:

ACTTGTACAG CGTCGACACC TC  22

(2) INFORMATION FOR SEQ ID NO:10:

(i) SEQUENCE CHARACTERISTICS:
    (A) LENGTH: 35 base pairs
    (B) TYPE: nucleic acid
    (C) STRANDEDNESS: single
    (D) TOPOLOGY: linear (i i) MOLECULE TYPE: Other nucleic acid;
    (A) DESCRIPTION: Synthetic DNA oligonucleotide (x i) SEQUENCE DESCRIPTION: SEQ ID NO:10:

GGGGTTTAAG CTTTACCACT GACTCCCCGG ACGTC  35

(2) INFORMATION FOR SEQ ID NO:11:

(i) SEQUENCE CHARACTERISTICS:
    (A) LENGTH: 13 base pairs
    (B) TYPE: nucleic acid
    (C) STRANDEDNESS: single
    (D) TOPOLOGY: linear (i i) MOLECULE TYPE: Other nucleic acid;
    (A) DESCRIPTION: Synthetic DNA oligonucleotide (x i) SEQUENCE DESCRIPTION: SEQ ID NO:11:

AGCTTGCGGC CGC  13

(2) INFORMATION FOR SEQ ID NO:12:

(i) SEQUENCE CHARACTERISTICS:
    (A) LENGTH: 9 base pairs
    (B) TYPE: nucleic acid
    (C) STRANDEDNESS: single (D) TOPOLOGY: linear (ii) MOLECULE TYPE: Other nucleic acid;
(A) DESCRIPTION: Synthetic DNA oligonucleotide (iv) ANTI-SENSE: YES (xi) SEQUENCE DESCRIPTION: SEQ ID NO:12:

GCGGCCGCA 9

(2) INFORMATION FOR SEQ ID NO:13:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

CGTCACCACC ATCCTGTTTT GCTGCAGGAA AACCCATATT TAATGCTGAA GGGGAACCAC 60

(2) INFORMATION FOR SEQ ID NO:14:

(i) SEQUENCE CHARACTERISTICS:
(A) LENGTH: 49 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

CGTCACCACC ATCCTGGAAA ACCCATATTT AATGCTGAAG GGGAACCAC 49

(2) INFORMATION FOR SEQ ID NO:15:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

CGTCACCACC ATCCTGGGGA ACCAC 25

(2) INFORMATION FOR SEQ ID NO:16:

(i) SEQUENCE CHARACTERISTICS:
(A) LENGTH: 34 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (xi) SEQUENCE DESCRIPTION: SEQ ID NO:16:

GGGGTTTAAG CTTGAGCGTC GTCCTCTTCC TGGT 34

(2) INFORMATION FOR SEQ ID NO:17:

(i) SEQUENCE CHARACTERISTICS:
(A) LENGTH: 34 base pairs
(B) TYPE: nucleic acid
(C) STRANDEDNESS: single
(D) TOPOLOGY: linear ( i ) MOLECULE TYPE: Other nucleic acid;
( A ) DESCRIPTION: Synthetic DNA oligonucleotide ( x i ) SEQUENCE DESCRIPTION: SEQ ID NO:17:

GGGGTTTAAG CTTGTGAAGA ACCACCAGAC GCCG    3 4